(12) United States Patent
Silverman et al.

(10) Patent No.: US 7,709,443 B2
(45) Date of Patent: May 4, 2010

(54) CYCLIC PEPTIDE ANTITUMOR AGENTS

(75) Inventors: Richard B. Silverman, Northbrook, IL (US); Shouxin Liu, Evanston, IL (US); Wenxin Gu, Evanston, IL (US); Thomas E. Adrian, Chicago, IL (US); Gerald A. Soff, Wilmette, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/962,168

(22) Filed: Oct. 8, 2004

(65) Prior Publication Data
US 2005/0159346 A1 Jul. 21, 2005

Related U.S. Application Data

(60) Provisional application No. 60/509,454, filed on Oct. 8, 2003.

(51) Int. Cl.
*A61K 38/00* (2006.01)
(52) U.S. Cl. .......................................... 514/9
(58) Field of Classification Search .................. 514/9
See application file for complete search history.

(56) References Cited

U.S. PATENT DOCUMENTS 6,797,807 B1* 9/2004 Blaschuk et al. ............ 530/300
2002/0128185 A1 9/2002 Shih

OTHER PUBLICATIONS

Lee et al, "Rapid, high-yield, solid-phase synthesis of the antitumor antibiotic sansalvamide A using a side-chain-tethered phenylalanine building block," Organic Letters, Nov. 16, 2000;2(23):3743-6.*
Suvorova, E.V. et al, Synthesis of poly(L-hydroxytryptophan), Mosk. Khim.-Tekhnol. Inst., Moscow, Russia, Zhurnal Obshchel Khimii (1993), 63(9), 2126-30, as shown in HCAPLUS in STN CAS Registry search report.*
Hwang Y., "Mechanism of inhibition of a poxvirus topoisomerase by the marine natural product sansalvamide A," Mol Pharmacol. Jun. 1999;55(6):1049-53.*
Gu W, "Solid-phase, Pd-catalyzed silicon-aryl carbon bond formation. Synthesis of sansalvamide a peptide," Org Lett. Nov. 14, 2002;4(23):4171-4174.*
Lee et al, Rapid, High Yeild, Solid-Phase Synthesis of the Antitumor Antibiotic Sansalvamide a using a Side-Chain-Tethered Phenylanine Building Block, Organic Letters, (2000), vol. 2, No. 23 3743-3746.*
L3 Answer 17 of 17 HCAPLUS.*
Hinds et al, "19F n.m.r. studies of conformational changes accompanying cyclic AMP binding to 3-fluorophenylalanine-contaning cyclic AMP receptor protein from *Escherichia coli*," Biochem. J. (1992) 287, 627-632.*

Kubyni, H, "Chemical Similarity and Biological Activities," J. Braz. Chem. Soc., vol. 132, pp. 717-726, 2002.*
Thronber, C.W. "Isosterism and Molecular Modification in Drug Design," Chem. Soc. Rev. (1979) vol. 8(4), pp. 563-580.*
Wormser et al, "Highly selective agonists for substance P receptor subtypes," The EMBO Journal (1986) vol. 5., No. 11, pp. 2805-2808.*
Ali et al, "Conformationally constrained peptides and semipeptides derived from RGD as potent inhibitors of the platelet fibrinogen receptor and platelet aggregation,".J Med Chem. Mar. 18, 1994;37(6):769-80.*
Fenical, William; Belofsky, Gilbert N.; Jensen, Paul R.; Sansalvamide: A New Cytotoxic Cyclic Depsipeptide Produced by a Marine Fungus of the Genus *Fusarium*. Center for Marine Biotechnology and Biomedicine. Scripps Institution of Oceanography, University of California, San Diego, La Jolla, CA 92093-0236; Tetrahedron Letters 40 (1999) 2913-2916, See p. 2913, formula 1, and p. 2915, last paragraph.
Silverman, Richard B. and Lee, Younghee; Rapid, High-Yield, Solid Phase, Synthesis of the Antitumor Antibiotic Sansalvamide A Using a Side-Chain-Tethered Phenylalanine Building Block. Department of Chemistry, Northwestern University, Evanston, Illinois 60208-3113; Organic Letters 2000 vol. 2. No. 23 3743-3746. See pp. 3743, paragraph 1, and formula 1.
Hwang, Young; Rowley, David; Rhodes, Denise; Gertsch, Jeff; Fenical, William; Bushman, Frederic, "Mechanism of Inhibition of a Poxvirus Topoisomerase by the Marine Natural Product Sansalvamide A", Molecular Pharmacology, Northwestern Univ Sci Engineering Lib; vol. 55, Issue 6,1049-1053 Jun. 1999.
Liu, Shouxin; Gu, Wenxin; Lo, Denise; Ding, Xian-Zhong; Ujiki, Michael; Adrian, Thomas E.; Soff, Gerald A.; Silverman, Richard B.; "N-Methylsansalvamide A Peptide Analogues. Potent New Antitumor Agents", American Chemical Society, 2005, J. Med. Chem. 2005, 48, 3630-3638.
Gu, Wenxin; Liu, Shouxin; Silverman, Richard B.; "Solid-Phase, Pd-Catalyzed Silicon-Aryl Carbon Bond Formation. Synthesis of Sansalvamide A Peptide"; American Chemical Society, 2002, Department of Chemistry and Drug Discovery Program, Northwestern University, Organic Letters 2002, vol. 4, No. 23 , 4171-4174.
Lee, Younghee; Silverman. Richard B.; "Silicon-based aromatic transferring linkers for traceless solid-phase synthesis of aryl-, polyaryl-, and heteroaryl-containing compounds", Elsevier Science Ltd. 2001, Tetrahedron 57 (2001) 5339-5352.
Hanford, Holly Anne; Wong, Christie A.; Kassan, Hallie; Cundiff, Deborah L; Chandel, Navdeep; Underwood, Suzanne; Mitchell Christopher A.; Soff, Gerald A.; "Angiostatin $_{4.5}$-mediated Apoptosis of Vascular Endothelial Cells", Northwestern University Feinberg School of Medicine, Department of Medicine, Divisions of Hematology/Oncology, Chicago, IL 60611; Cancer Research 63, 4275-4280, Jul. 15, 2003.

* cited by examiner

*Primary Examiner*—Anish Gupta
*Assistant Examiner*—Thomas S Heard
(74) *Attorney, Agent, or Firm*—Reinhart Boerner Van Deuren s.c.

(57) ABSTRACT

Cyclic peptide compounds and derivatives thereof having antitumor activity as shown by treatment of human melanoma, pancreatic, breast, prostate cancer cells.

12 Claims, 5 Drawing Sheets

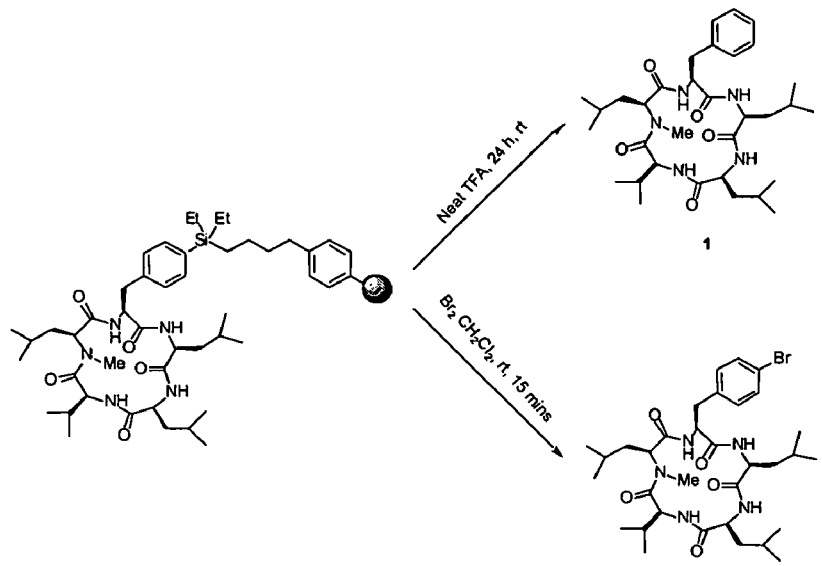
Figure 2
Figure 3
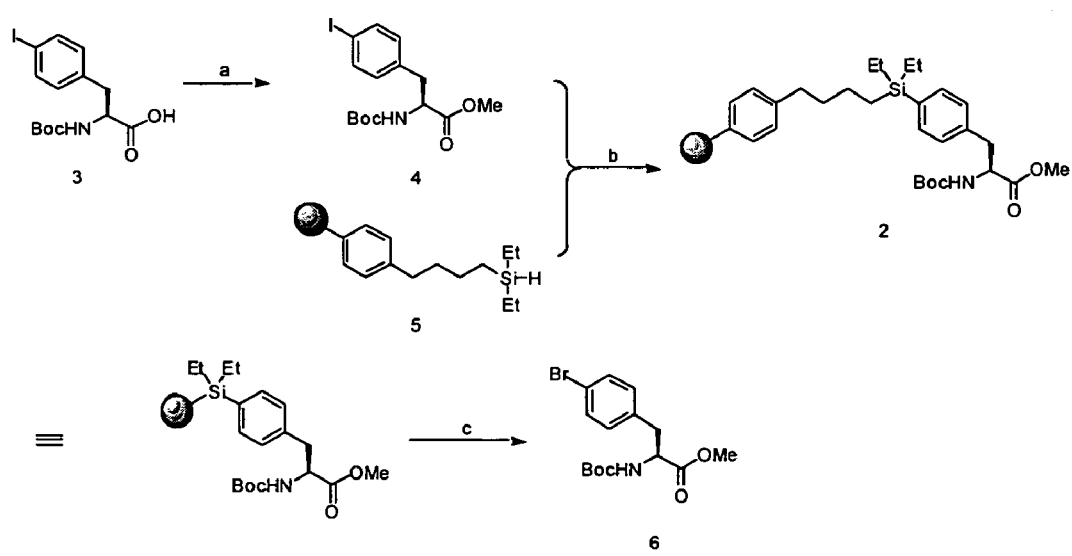

CYCLIC PEPTIDE ANTITUMOR AGENTS

This application claims priority benefit of application Ser. No. 60/509,454 filed Oct. 8, 2003, the entirety of which is incorporated herein by reference.

BACKGROUND OF THE INVENTION

Sansalvamide A is produced by a marine fungus of the genus *Fusarium* found on Little San Salvador Island, Bahamas. It was isolated as reported in the literature (Fenical et al., *Tetrahedron Lett.* 1999, 40, 2913-16) and shown to have cytotoxic activity against several cancer cell lines. A study of the mechanism of action of this natural product in the poxvirus *molluscum contagiosum* virus showed it to be an inhibitor of topoisomerase I.

Notwithstanding the promise of sansalvamide A, many cancer disease states remain without an effective chemotherapy. For instance, most patients with pancreatic cancer die within six months of diagnosis: mortality and incidence are almost equal. Pancreatic cancer has recently overtaken prostate cancer as the third leading cause of cancer death in men (after lung and colon). It is also the fourth leading cause of cancer death in women (after lung, breast, and colon). Less than 20% of patients are diagnosed early enough in the disease process for potentially curative surgery. Even in these patients, however, the survival rate is still low. Gemcitabine is currently the first-line chemotherapeutic agent used in patients with pancreatic cancer, but it has little impact on survival.

Sansalvamide A is a cyclic depsipeptide with lipophilic properties affording it protease resistance and membrane permeability, allowing for greater oral bioavailability. The core ring structure restricts bond rotation and creates a more rigid conformation that results in a higher binding affinity and longer half-life in vivo. However, as shown below, sansalvamide A is somewhat limited in its potency. The search for an effective antitumor agent, for pancreatic and other cancer disease states, remains an on-going concern in the art.

BRIEF DESCRIPTION OF THE DRAWINGS

FIG. 2. Schematic reactions illustrating peptide cleavage from a solid-support.

FIG. 3. Solid phase silicon-aryl bond formation (and cleavage) in preparation of the compounds of this invention. Reagents and conditions: (a) MeI, NaHCO$_3$, DMF, rt, 98%; (b) Pd catalyst, phosphine ligand, base, solvent; (c) Br$_2$ in CH$_2$Cl$_2$, 15 min.

SUMMARY OF THE INVENTION

Figure 1A:
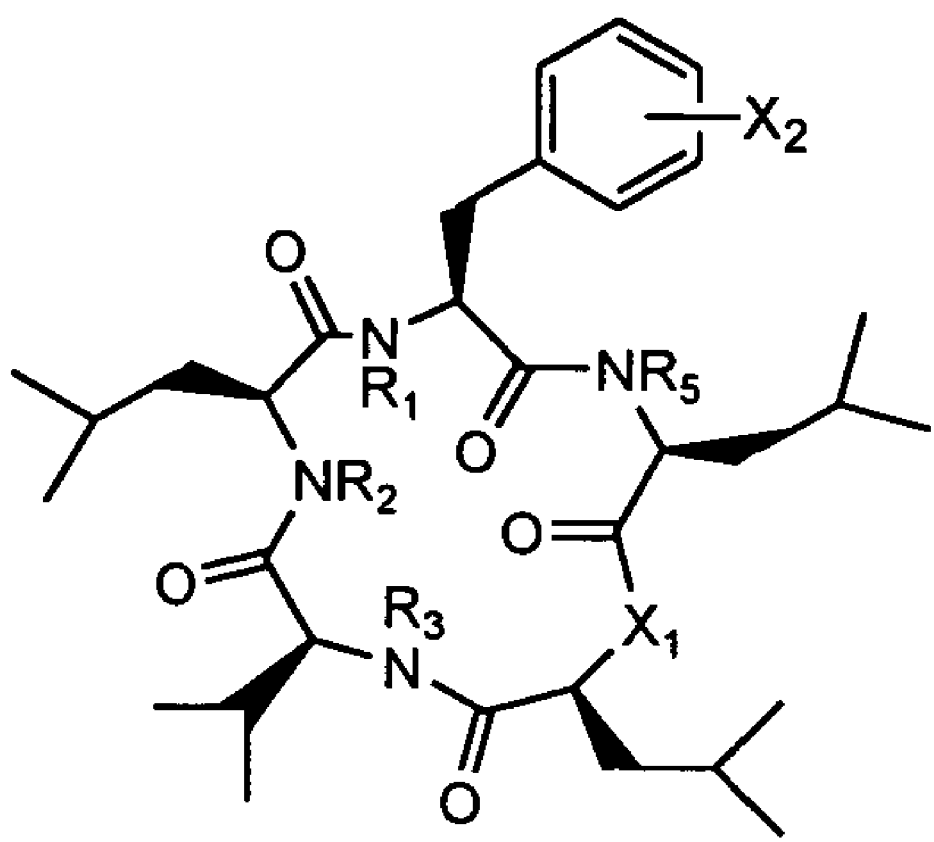
FIG. 1A. A non-limiting structure of cyclic peptide compounds of this invention.

In light of the foregoing, it is an object of the present invention to provide compounds and/or methods for their preparation and use as antitumor agents, thereby overcoming various deficiencies and shortcomings of the prior art, including those outlined above.

It is an object of the present invention to provide a peptide analog of sansalvamide A to enhance cytotoxic activity and improve potency against various cancer cell lines.

It is another object of the present invention to provide one or more derivatives of the peptide analog of sansalvamide A, to further assess and/or enhance cytotoxic activity as compared to either sansalvamide A or the peptide analog.

It is another object of the present invention to provide one or more cyclic peptide compounds of the sort described herein to inhibit cancer cell proliferation. In particular, without limitation, it is a related object to provide a range of such compounds for use in the treatment of human pancreatic cancer, human breast cancer, human prostate cancer and human melanoma, such treatment as can be evidenced by the cellular inhibition of DNA synthesis by inhibition of caspase-3 or by induction of apoptosis.

Other objects, features, benefits and advantages of the present invention will be apparent from this summary and its descriptions of various embodiments, and will be readily apparent to those skilled in the art having knowledge of various antitumor compounds, their design and synthesis. Such objects, features, benefits and advantages will be apparent from the above as taken into conjunction with the accompanying examples, data, figures, incorporated references and all reasonable inferences to be drawn therefrom.

In part, the present invention comprises cyclic peptide compounds of a formula

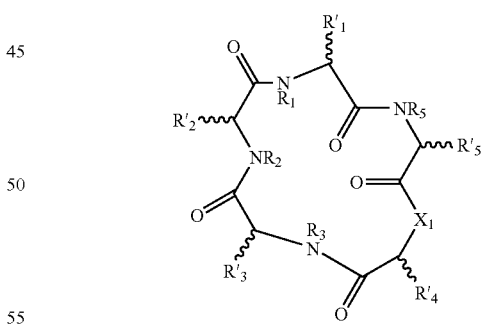

wherein each of $R_1$-$R_5$ can be independently selected from hydrogen and alkyl moieties; $X_1$ is either O or $NR_4$; $R_1'$ is $X_2ArCH_2$ wherein $X_2$ is hydrogen or, alternatively, a halide, hydroxy or alkyl positional substituent, when $X_1$ is $NR_4$, or either halide or alkyl when $X_1$ is O, and Ar can be selected from aryl and heteroaromatic moieties; and each of $R_2'$-$R_5'$ is independently selected from $R_1'$, and the α-substituents of various amino acids, including but not limited to CH$_3$-(Ala), (CH$_3$)$_2$CH-(Val), (CH$_3$)$_2$CHCH$_2$-(Leu), CH$_3$CH$_2$(CH$_3$)CH-(Ile) and CH$_3$S CH$_2$CH$_2$-(Met) moieties.

In certain embodiments, $X_1$ is $NR_4$ and $R_1'$ is $X_2ArCH_2$—, where $X_2$ is selected from hydrogen and halide. In certain other embodiments, each of $R_2'$-$R_5'$ can be independently selected from $(CH_3)_2CHCH_2$— and $(CH_3)_2CH$—. Regardless, in such embodiments, at least one of $R_1$-$R_5$ can be alkyl. More specifically, in certain embodiments, each of $R_2'$, $R_4'$ and $R_5'$ are $(CH_3)_2CHCH_2$— and $R_3'$ is $(CH_3)_2CH$— and $R_3'$ is $(CH_3)_2CHCH_2$— and $R_3'$ is $(CH_3)_2CH$—. As illustrated below, $R_1'$-$R_5'$ can have a syn relationship. In such compounds, at least one of $R_1$-$R_5$ is methyl.

For purposes of the present compounds and/or methods, the designation "Ar," unless otherwise indicated, will be understood as having the meaning ascribed thereto by those skilled in the art or otherwise indicated with respect thereto; that is, "Ar" means aryl, e.g., phenyl, naphthyl, anthryl, phenanthryl and other polycyclic condensed aromatic moieties, together with heteroaromatic moieties including but not limited to indolyl, pyridinyl, furanyl, thiophenyl and thiazolyl. Such groups can be incorporated into the $R_1'$ moieties of the present compounds using the synthetic procedures described herein, straightforward modifications thereof as would be understood by those skilled in the art and/or techniques of the sort described in U.S. Pat. No. 6,416,861, in particular but without limitation to columns 20-22 and the naphthylalanine, thienylalanine and phenethylglycine analogues described therein, such patent incorporated herein by reference in its entirety.

Figure 1B:
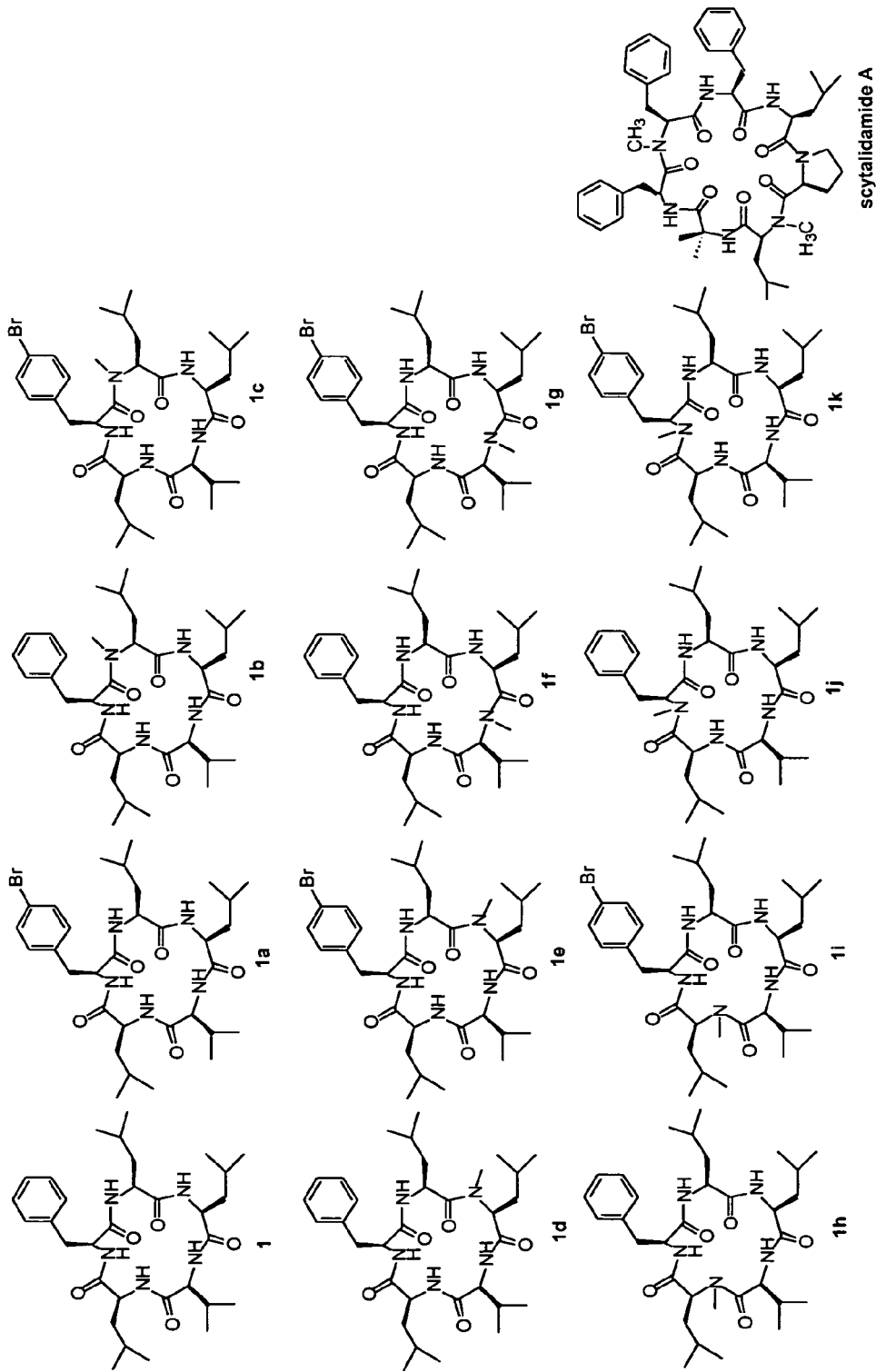
FIG. 1B. Cyclic peptides, in accordance with the structure of FIG. 1, also showing for purpose of comparison the structure of a reference natural product.

Accordingly, the present invention comprises a range of cyclic compounds, including but not limited to compounds represented by the structural formulae of FIGS. 1A and 1B. More specifically, with reference to FIG. 1A, compounds of this invention can include various phenyl-substituted analogs of the natural product sansalvamide A (see, e.g., Table 1), as can be prepared as provided herein or known in the art through modification of the natural product synthesis and/or appropriate solid-phase techniques described in conjunction with this invention. With further reference to FIG. 1A and as shown in FIG. 1B, numerous N-methyl analogs and/or their substituted-phenyl derivatives are also contemplated within the scope of this invention. As described more fully below, the N-methyl analogs can be prepared through use of the corresponding N-methyl amino acid. Alternatively, using analogous synthetic procedure(s), multiple methylations and the resulting compounds can be achieved. The per-methylated analog can be prepared in a similar fashion, with acknowledgement of the difficulty inherent in cyclization with a secondary amine. The corresponding phenyl-substituted derivatives are available by cleavage from a solid support, alternately substituted as can be provided through use of the appropriate halogen or strong acid reagent(s), as shown in FIG. 2 and further demonstrated herein.

In conjunction with its compositional aspects, the present invention also demonstrates a solid-phase methodology for palladium-catalyzed silicon-aryl carbon bond formation. As illustrated below, a phenylalanine silane resin can be prepared directly from the corresponding protected iodo-substituted phenylalanine with butyl diethylsilane polystyrene, in one step. The rapid and high-yield solid phase synthesis of sansalvamide A peptide illustrates but one use of this inventive methodology (see, FIGS. 3 and 4). Other embodiments of this methodology are available, as demonstrated below, for preparation of the various N-methyl analogs and/or the corresponding phenyl-substituted derivatives. (See, e.g., Scheme 2, below, and related examples).

The cyclic peptide is about 10 times more potent, and the N-methyl bromo-substituted analog (see Table 1 below) is almost 100 times more potent, than sansalvamide A toward HCT-116 colon carcinoma cell line. Sequential replacement of each amino acid of sansalvamide A with the corresponding N-methyl amino acid can determine position(s) for N-methyl modification. More than one methylation site may increase potency, and multiple N-methyl amino acids can be incorporated, as mentioned above. More broadly, N-alkylation can be optimized in a similar manner.

TABLE 1

Activity of Sansalvamide A Analogs in HCT-116 (human colon carcinoma) Bioassay

| Compound | sansalvamide A | sansalvamide A iodide |
|---|---|---|
| $IC_{50}$* (µg/mL) | 9.8 | 11.3 |

TABLE 1-continued

Activity of Sansalvamide A Analogs in HCT-116 (human colon carcinoma) Bioassay

| Compound | sansalvamide A bromide | sansalvamide A peptide (Cpd. 1) |
|---|---|---|
| | 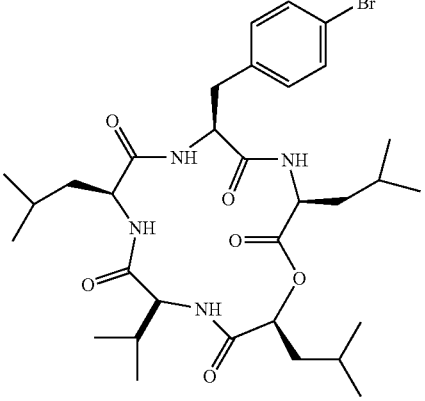 | 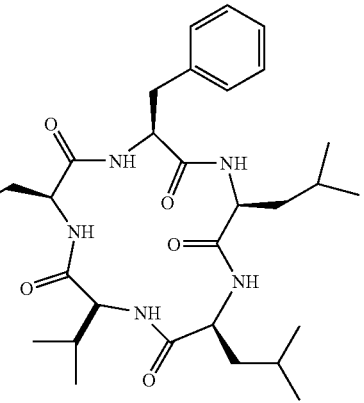 |
| IC$_{50}$* (μg/mL) | 4.5 | 0.98 |

| Compound | N-Me sansalvamide A bromide (Cpd. 1e) |
|---|---|
| | 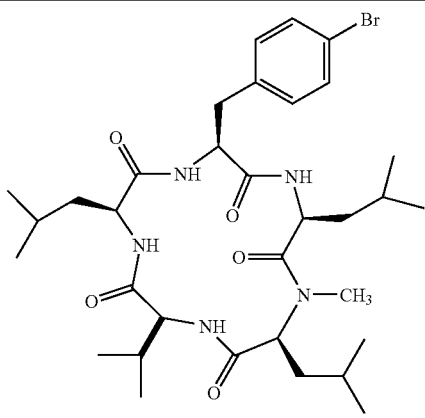 |
| IC$_{50}$* (μg/mL) | 0.11 |

*By comparison, in this assay etoposide (VePesid) had an IC$_{50}$ of 1.5 μg/mL

It is reasonable that the phenylalanine residue binds in a hydrophobic pocket of the target protein. The changes to the phenyl group noted in Table 1 indicated that para-iodination decreased activity, but para-bromination increased it (relative to the sansalvamide A). Because the para-bromide showed increased activity, the para-chloro, para-fluoro, para-alkyl and like analogs are also contemplated within the scope of this invention. Likewise, other o-, m- or p-substituted (halo, aryl, alkyl, etc.) phenylalanine reactants also can be used to prepare the corresponding derivatives. Other positional isomers are available through choice of reactants and/or reagents, using comparable reaction sequences, as would be known by those skilled in the art made aware of this invention. To increase water solubility, the phenylalanine residue can be substituted with either pyridinylmethylglycine or thiazolidinylmethylglycine. (Two regioisomers of the latter are commercially available, as are all of the protected amino acid analogs used in conjunction with this invention from RSP Amino Acids, PepTech, ChiroTech, or Advanced ChemTech.) Additional binding interactions are possible with these analogs as well. Such modified groups can be incorporated into both the cyclic depsipeptide (i.e., $X_1$=$O_1$ in FIG. 1A) as well as the cyclic peptide analogs. As potency increases are observed with such heterocyclic analogs, other heterocyclic phenyl isosteres (e.g., furanyl, thiophenyl, pyrimidinyl, etc.) can be used with variable effect. In addition to modifications of the phenylalanine residue, each of the other residues can be sequentially substituted with, for instance, hydrophobic analogs.

Regarding the synthesis of such peptides and halophenyl sansalvamide A derivatives, the traditional method of generating arylsilanes on a solid-phase involves reaction of chlorosilanes with aryllithium reagents, but is restricted to substrates lacking sensitive functional groups. Compounds of this invention were prepared using a novel and convenient method for the synthesis of a polymer-bound aryl building blocks. A silicon-aryl carbon bond was formed using the reaction of a polystyrene hydrosilane with iodophenylalanine under mild palladium-catalyzed reaction conditions. The resin-bound phenylalanine building block was then used for the synthesis of the first analog of the natural cyclic depsipeptide sansalvamide A, namely, the sansalvamide A cyclic peptide compound 1, and as well as the corresponding N-methyl derivatives. This methodology is a convenient general approach for the generation of resin-bound arylsilanes directly from aryl halides.

The reaction of butyldiethylsilane polystyrene with Boc-4-iodophenylalanine methyl ester was investigated using different palladium catalysts in combination with different phosphines. As shown in FIG. 3, esterification of Boc-4-iodophenylalanine with iodomethane using sodium bicarbonate as a base afforded Boc-4-iodophenylalanine methyl ester (4). The palladium-catalyzed reaction of 4 and commercially available butyl diethylsilane polystyrene (5, PS-DES-S1H) under various reaction conditions afforded the phenylalanine silane linker (2), as described in Table 2 below. The loading level of 2 was determined by weighing the product of cleavage of 2 with bromine in methylene chloride. No reaction was observed using tetrakis-(triphenylphosphine)-palladium(0) (Pd(PPh$_3$)$_4$) as the catalyst, with either sodium carbonate or potassium acetate as the base both at room temperature and 105° C. However, the reaction was catalyzed by tris-(dibenzyleneacetone) dipalladium(0) chloroform adduct (Pd$_2$(dba)$_3$.CHCl$_3$). In the presence of an added bulky phosphine (P(o-Tol)$_3$), reaction was less than optimal (entries 4-6). KOAc proved to be a more effective base than the tertiary amine DIPEA. The use of amide solvents such as NMP and DMF also promotes the success of this silylation reaction. An especially effective base for this catalytic reaction was KOAc in the presence of Pd$_2$(dba)$_3$.CHCl$_3$.

Figure 4:
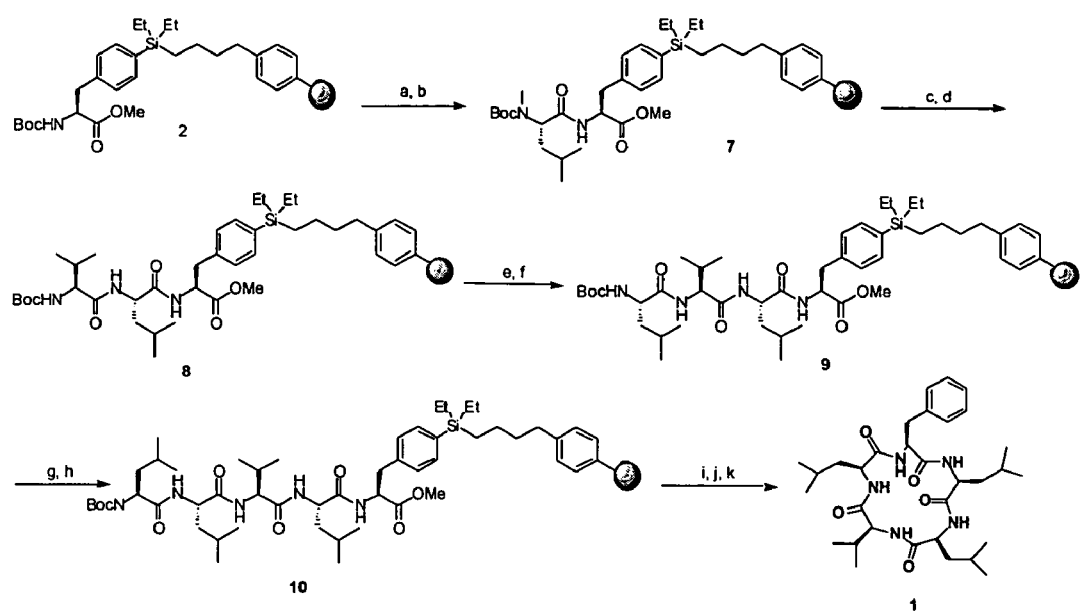
FIG. 4. Sequential peptide synthesis enroute to the cyclic compounds of this invention. Reagents and conditions: (a) 50% TFA in CH$_2$Cl$_2$, rt, 15 min; (b) Boc-Leu-OH (5 equiv), HATU (5 equiv), DIPEA (15 equiv), NMP, 6 h; (c) 50% TFA in CH$_2$Cl$_2$, rt, 15 min; (d) Boc-Val-OH (5 equiv), HATU (5 equiv), DIPEA (15 equiv), NMP, 6 h; (e) 50% TFA in CH$_2$Cl$_2$, rt, 15 min; (f) Boc-Leu-OH (5 equiv), HATU (5 equiv), DIPEA (15 equiv), NMP, 6 h; (g) 50% TFA in CH$_2$Cl$_2$, rt, 15 min; (h) Boc-Leu-OH (5 equiv), HATU (5 equiv), DIPEA (15 equiv), NMP, 6 h; (i) LiOH (5 equiv), THF/H$_2$O (7:1); (j) 50% TFA in CH$_2$Cl$_2$, rt, 15 min; (k) PyBOP (5 equiv), DIPEA (15 equiv), NMP, 24 h; (l) neat TFA, 24 h, rt.

As shown in FIG. 4, synthesis of sansalvamide A peptide analog 1 was initiated from the N-terminus of phenylalanine silane linker 2. A low loading level (0.09 mmol/g) of 2 was selected to avoid problems of oligomer formation during the final cyclization step. Boc protecting groups were employed for peptide chain extensions to reduce the possibility of diketopiperazine formation, which is prevalent when Fmoc deprotection is used. Although oxazolone or oxazolonium ion formation occurs when acylating amine groups, and Boc-oxazolonium ions can decompose to N-carboxyanhydride derivatives much more readily than the corresponding Cbz- or Fmoc-protected derivatives, the undesired byproducts can be washed out after every coupling reaction. Deprotection of the Boc group of 2 followed by reaction of the resulting amine with Boc-Leu-OH and DIPEA, in the presence of a highly effective activating reagent HATU in NMP as a solvent, afforded polymer-bound dipeptide 7. Elongation of the peptide chain to the linear peptide 10 was accomplished by stepwise coupling of the appropriate Boc-protected amino acids under analogous conditions. Deprotection of the methyl ester and Boc protecting groups of 10 gave the resin-bound linear peptide. To avoid guanidine formation when employing an excess of the uronium salt HATU during the activation of the carboxylate acid group of the linear pentapeptide, the phos-

TABLE 2

Reaction Conditions of Butyl Diethylsilane Polystyrene (PS-DES)
(Loading Level 1.45 mmol/g) with Boc-4-IodophenylalnineMethylEster

| entry | Pd catalyst | ligand | base | solvent | temperature (° C.) | loading level (mmol/g) |
|---|---|---|---|---|---|---|
| 1 | Pd(PPh$_3$)$_4$ | | Na$_2$Co$_3$ | NMP | 25 | |
| 2 | Pd(PPh$_3$)$_4$ | | Na$_2$CO$_3$ | NMP | 105 | |
| 3 | Pd(PPh$_3$)$_4$ | | KOAc | NMP | 105 | |
| 4 | Pd$_2$(dba)$_3$—CHCl$_3$ | P(o-tol)$_3$ | DIPEA | NMP | 25 | 0.1 |
| 5 | Pd$_2$(dba)$_3$—CHCl$_3$ | P(o-tol)$_3$ | DIPEA | NMP | 105 | 0.2 |
| 6 | Pd$_2$(dba)$_3$—CHCl$_3$ | P(o-tol)$_3$ | KOAc | NMP | 105 | 0.3 |

As mentioned above, the natural depsipeptide sansalvamide A was found to have significant cancer cell cytotoxicity, with a mean IC$_{50}$ value of 27.4 µg/mL against the National Cancer Institute's 60 cell-line panel, and an in vitro value of 9.8 µg/mL toward HCT-116 colon carcinona. It was thought that modification, including alteration of the lactone linkage of the depsipeptide, would improve activity.

Sansalvamide A

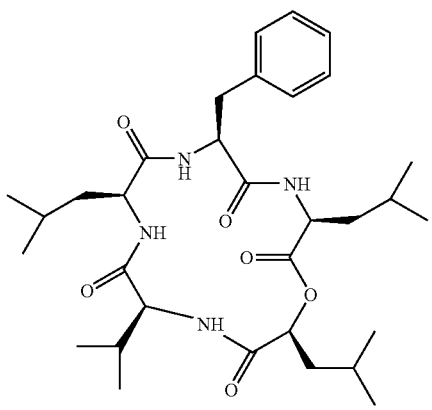

phonium salt PyBOP was substituted for HATU in the cyclization step. Sansalvamide A peptide 1 was released from the resin in an overall 66% yield (based on the loading level of 2) using neat TFA for 24 h. (See, FIG. 2) HPLC analysis proved the cyclic peptide to be 94% pure. The target molecule was characterized with $^1$H NMR, $^{13}$C NMR, and high-resolution mass spectrum. (See, examples 12-12k below.)

Based on the structure of sansalvamide A, in accordance with this invention, a library of compounds can be constructed. In particular, without limitation, compounds 1-1k were designed, as shown in FIG. 1B. The five amide groups of sansalvamide A peptide can be, alternatively, N-methylated (or alkylated). At the same time, by different cleavage methods, their bromides (or other halides) can be produced as well.

Scheme 1 shows a general synthetic approach for every resin bound N-methylated sansalvamide A peptide. Starting from the polymer bound phenylalanine building block, the corresponding amino acid was coupled according to the sequence of sansalvamide A, except that a methyl group can Scheme 1
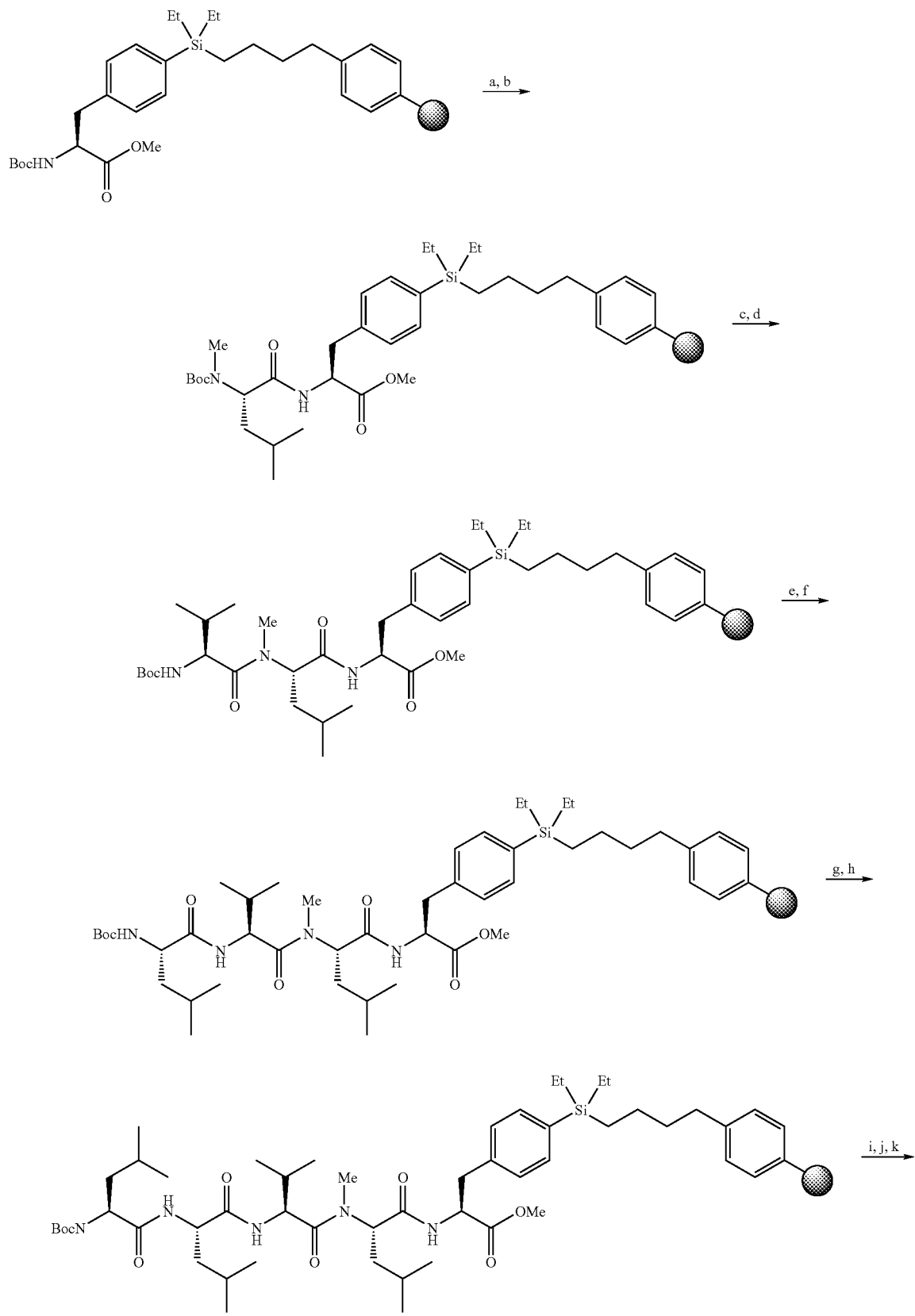

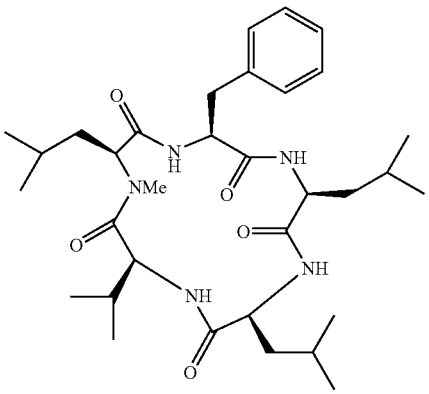

be incorporated into the structure at each of the amide bonds.

Reagents and conditions: (a) 50% TFA in $CH_2Cl_2$, rt, 15 min; (b) Boc-MeLeu-OH (5 equiv), HATU (5 equiv), DIPEA (15 equiv), NMP, 6 h; (c) 50% TFA in $CH_2Cl_2$, rt, 15 min; (d) Boc-Val-OH (5 equiv), HATU (5 equiv), DIPEA (15 equiv), NMP, 6 h; (e) 50% TFA in $CH_2Cl_2$, rt, 15 min; (f) Boc-Leu-OH (5 equiv), HATU (5 equiv), DIPEA (15 equiv), NMP, 6 h; (g) 50% TFA in $CH_2Cl_2$, rt, 15 min; (h) Boc-Leu-OH (5 equiv), HATU (5 equiv), DIPEA (15 equiv), NMP, 6 h; (i) LiOH (5 equiv), $THF/H_2O$ (7:1); (j) 50% TFA in $CH_2Cl_2$, rt, 15 min; (k) PyBOP (5 equiv), DIPEA (15 equiv), NMP, 24 h.

With reference to FIG. 2, resin bound N-methylated sansalvamide A peptides can be cleaved with neat TFA to afford the corresponding cyclic peptides. Cleavage of the cyclic peptides from the resin with bromine afforded the cyclic peptide bromides. Compounds 1-1i can be synthesized from a polymer bound phenylalanine building block 2, while compounds 1j and 1k can be prepared from an N-methylated polymer bound phenylalanine building block 2a.

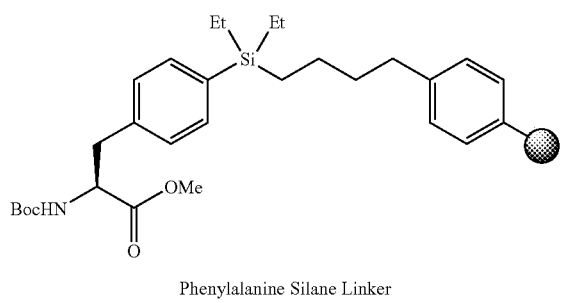

Phenylalanine Silane Linker

2

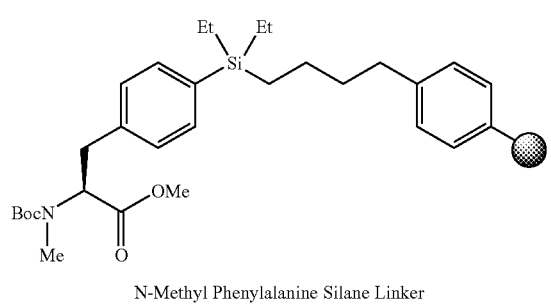

N-Methyl Phenylalanine Silane Linker

2a

Referring to Scheme 2, below, N-Methylated Boc-4-iodophenylalanine methyl ester 16 was synthesized for the preparation of the N-methylated polymer bound phenylalanine building block. Starting from 4-iodophenylalnine 12, reaction of 12 with trifluoroacetic anhydride using triethyl amine as a base afforded 13, which was not further purified and used in the next step directly. The methylation of amide and acid groups of 13 were accomplished in one pot by treating 13 with iodomethane and $K_2CO_3$ in acetone at room temperature to afford the expected N-methyl-N-trifluoroacetyl-4-iodophenylalanine methyl ester 14 in an 87% yield in two steps. Hydrolysis of 14 afforded N-methylated 4-iodophenylalanine 15 in a 93% yield. Finally the amine group of 15 was protected with $Boc_2O$ to afford 16 in an 89% yield, which was coupled to the butyl silane polystyrene to afford the expected N-methyl-phenylalanine silane linker 2a.

With reference to Schemes 1 and 2, a range of homologous N-alkylated (e.g., ethyl, etc.) compounds can be prepared as described herein with corresponding modification of reagents and reaction conditions, as would be known to those skilled in the art without undue experimentation. Likewise, while certain embodiments are illustrated with compounds prepared from L-amino acids, it will be understood that the cyclic peptides of this invention can be prepared from D-amino acids or various mixtures of D- and L-amino acids. Such compounds can further comprise one or more N-alkyl and/or aryl-substituents, as described above.

Scheme 2

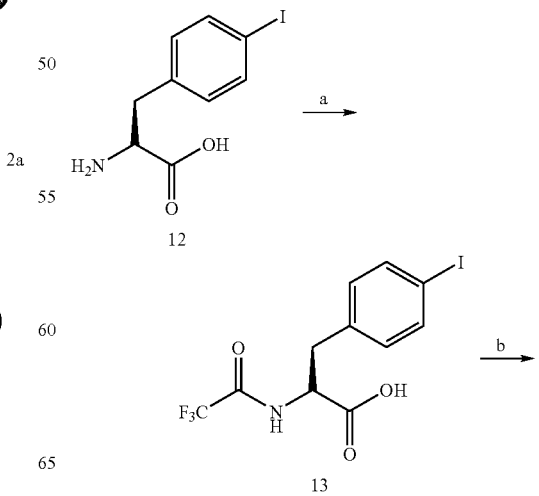

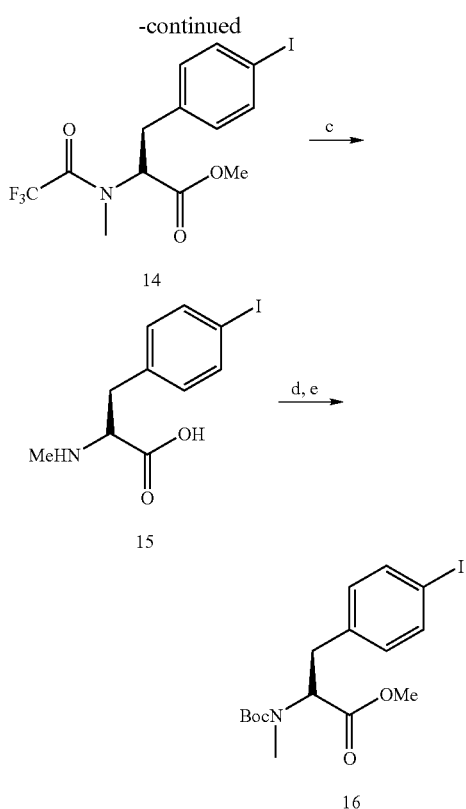

Reagents and conditions: (a). (F$_3$CCO)$_2$O, TEA, acetone, rt; (b). MeI, K$_2$CO$_3$, acetone, rt; (c). K$_2$CO$_3$, acetone/H$_2$O, 40° C.; (d). Boc$_2$O, TEA; (e). MeI, K$_2$CO$_3$, acetone, rt.

EXAMPLES OF THE INVENTION

The following non-limiting examples and data illustrate various aspects and features relating to the compounds and/or methods of the present invention, including the use of either derivatives of sansalvamide A, peptide analogues of sansalvamide A and/or derivatives thereof, such compounds as are available through the synthetic methodologies described herein. In comparison with the prior art, the present compounds and related methods provide results and data which are surprising, unexpected and contrary thereto. While the utility of this invention is illustrated through the use of several compounds, it will be understood by those skilled in the art that comparable results are obtainable with various other compounds, as are commensurate with the scope of this invention.

Abbreviations used: DIPEA, diisopropylethylamine; DMF, dimethylformamide; HATU, O-(7-azabenzotriazol-1-yl)-N,N, N'N'-tetramethyluronium hexafluorophosphate; NMP, N-methylpyrrolidinone. PyBOP, Benzotriazole-1-yl-oxy-tris-pyrrolidine-phosphonium hexafluorophosphate.

General Methods. Conventional organic solvents were purchased from Fisher. All of the reagents were purchased from Aldrich Chemical Co and were used without further purification unless stated otherwise. Butyl diethylsilane polystyrene (PE-DES-SiH, 1.45 mmol/g) was purchased from Argonaut Technologies Inc. Methylene chloride was distilled under N$_2$ from calcium hydride. Flash chromatography was performed with Merck silica gel (230-400 mesh). TLC plates (silica gel 60-F254) were purchased from VWR Scientific. All $^1$H NMR spectra were recorded on Varian Gemini 300 MHz, Mercury 400, or Inova 500 spectrometers (75, 100, or 125 MHz for $^{13}$C NMR spectra). Chemical shifts (δ) are reported downfield from tetramethylsilane (Me$_4$Si) in parts per million (ppm). Compounds were visualized with a ninhydrin spray reagent or a UV/vis lamp. Mass spectra were recorded either on a VG Instrument VG70-250SE high-resolution mass spectrometer (ESI) or on a Micromass Quattro II spectrometer (APCI).

Example 1

N-Boc-4-iodophenylalanine methylester (4). To a solution of 5.02 g (12.8 mmol) of N-Boc-4-iodophenylalanine in 60 mL of DMF was added NaHCO$_3$ (1.42 g, 16.9 mmol) followed by methyl iodide (3.0 mL, 48.2 mmol). The mixture was stirred under argon for 40 h at room temperature. After this time, 150 mL of ethyl acetate was added, and the mixture was washed with 3×100 mL of deionized water. The organic layer was separated, dried over Na$_2$SO$_4$, and concentrated under vacuum to yield 5.80 g of a yellow oily solid. The crude product was purified by flash chromatography (1:5 ethyl acetate:hexanes) to afford a white solid (4.72 g, 91%). mp 79-80° C.; $^1$H NMR (400 MHz, CDCl$_3$) δ 1.43 (s, 9 H), 3.04 (2 dd, J=4.8 Hz, 12.8 Hz), 3.72 (s, 3 H), 4.58 (m, 1 H), 4.97 (brs, NH, 1 H), 6.88 (d, J=7.8 Hz, 2 H), 7.62 (d, J=7.8 Hz, 2 H); HRMS (ESI, M+1) calcd for C$_{15}$H$_{21}$INO$_4$ 406.0510, found 406.0515.

Example 2

Phenylalanine silane linker (2). Typically, to a solution of N-Boc-4-iodophenylalanine methylester (4, 800 mg, 2 mmol) in NMP (20 mL) was added butyl diethylsilane polystyrene (5, PE-DES-SiH, 1 g, 1.45 mmol/g) and KOAc (300 mg, 0.3 mmol). The reaction mixture was deaerated by bubbling with a slow stream of argon for 15 min. After the addition of Pd$_2$(dba)$_3$·CHCl$_3$ (110 mg, 0.1 mmol), the reaction flask and reflux condenser were wrapped with aluminum foil, and the mixture was stirred at 110° C. for 24 h. After being cooled to room temperature and washed with CH$_2$Cl$_2$, DMF, 1 N HCl/THF (1:7, 30 min), MeOH, and CH$_2$Cl$_2$, an aliquot of the resin (200 mg) was treated with a solution of Br$_2$ (15 μL) in CH$_2$Cl$_2$ (10 mL) for 20 min. The cleavage solution was filtered and the resin was rinsed with CH$_2$Cl$_2$ (5 mL). Concentration of the combined filtrates gave N-Boc-4-bromophenylalanine methylester (6; the loading level of 2 was determined to be 0.8 mmol/g); $^1$H NMR (400 MHz, CDCl$_3$) δ 1.43 (s, 9 H), 3.05 (2 dd, J=6.0 Hz, 13.6 Hz), 3.73 (s, 3 H), 4.57 (m, 1 H), 4.99 (d, J=7.6 Hz, NH, 1 H), 7.01 (d, J=8.0 Hz, 2 H), 7.42 (d, J=8.0 Hz, 2 H); HRMS (ESI, M+1) calcd for C$_{15}$H$_{21}$BrNO$_4$ 358.0648 and 360.0628, found 358.0654 and 360.0635.

Example 3

Solid-phase synthesis of sansalvamide A peptide (1) using phenylalanine silane linker 2. A suspension of resin 2 (1 g, 0.09 mmol/g) was treated with 50% TFA in CH$_2$Cl$_2$ (20 mL) for 15 min, then washed with CH$_2$Cl$_2$, 0.1 N HCl/THF, MeOH, and DMF. The washed resin was suspended in NMP (20 mL), treated with Boc-Leu-OH (5 eq), HATU (5 eq), and DIPEA (15 eq) for 6 h. After being washed with DMF, 0.1 N HCl/THF, MeOH, and DMF, the resin was cycled through the same set of conditions for deprotection, washing, coupling, and washing as above using Boc-Val-OH (5 eq), Boc-Leu- OH (5 eq), and Boc-Leu-OH (5 eq) successively in the peptide elongation. After being washed with DMF, 0.1 N HCl/THF, MeOH, and DMF, the deprotected linear peptide bound to the resin was shaken with LiOH (5 eq) in THF/H$_2$O (7:1, 20 mL) at room temperature for 12 h. After being washed with DMF, 0.1 N HCl/THF, MeOH, and DMF, the resin was treated with 50% TFA in CH$_2$Cl$_2$ (20 mL) for 15 min, then washed with CH$_2$Cl$_2$, 0.1 N HCl/THF, MeOH, and DMF. Cyclization was carried out by treatment of the resin in NMP (20 mL) with PyBOP (5 eq), and DIPEA (15 eq) for 24 h followed by washing with DMF, 0.1 N HCl/THF, MeOH, and CH$_2$Cl$_2$. The resin was then treated with neat TFA for 24 h at room temperature to release the cyclic peptide. The cleavage solution was filtered, and the resin was rinsed with CH$_2$Cl$_2$ (20 mL). Concentration of the combined filtrates gave the crude product, which was filtered through a short silica gel plug with ethyl acetate to afford sansalvamide A peptide (1, 34 mg, 66%). The purity was determined to be greater than 90% based on HPLC separation; HRMS (APCI, M+1) calcd for C$_{32}$H$_{52}$N$_5$O$_5$ 586.396, found 586.395; $^1$H NMR (500 MHz, CD$_3$OD) δ 0.82 (d, J=6.5 Hz, 3 H), 0.85 (d, J=6.5 Hz, 3 H), 0.90 (d, J=6.5 Hz, 3 H), 0.96 (d, J=6.5 Hz, 9 H), 1.00 (d, J=6.0 Hz, 6 H), 1.38-1.41 (m, 1 H), 1.44-1.50 (m, 2 H), 1.63-1.66 (m, 2 H), 1.72-1.75 (m, 2 H), 1.81-2.00 (m, 3 H), 2.04-2.09 (m, 1 H), 3.07 (dd, J=14.0 Hz, 11.0 Hz, 1 H), 3.24 (dd, J=14.0 Hz, 4.5 Hz, 1 H), 3.71 (brs, 1 H), 4.05 (d, J=8.0 Hz, 1 H), 4.54 (dd, J=11.0 Hz, 4.5 Hz, 1 H), 4.71 (dd, J=9.0 Hz, 5.0 Hz, 1 H), 7.25 (m, 5 H); $^{13}$C NMR (100 MHz, CD$_3$OD) δ 18.7, 20.0, 22.1, 22.2, 22.4, 23.2, 23.4, 23.6, 26.0, 26.1, 26.2, 32.2, 38.0, 39.5, 41.3, 41.7, 52.4, 56.4, 58.2, 60.5, 61.7, 128.0, 129.6, 129.7, 130.3, 138.8, 171.5, 173.0, 173.7, 174.0, 174.1.

Example 4

N-Trifluoroacetyl-4-iodophenylalanine (13)

To a solution of 4-iodophenylalanine (12, 2 mmol, 0.58 g) and triethylamine (16 mmol, 4.6 mL) in acetone was added slowly trifluoroacetic anhydride (16 mmol, 2.3 mL) with stirring at room temperature. The mixture was stirred overnight and then concentrated. The residue was dissolved in 1 N HCl (20 mL), then extracted with ethyl acetate (3×20 mL), and the organic layer was washed with brine. The solution was dried over anhydrous Na$_2$SO$_4$ and concentrated to give crude product (0.73 g) which was taken on without further purification.

Example 5

N-Methyl-N-trifluoroacetyl-4-iodophenylalanine methyl ester (14)

To a solution of above product (0.73 g) in 50 mL of anhydrous acetone was added anhydrous K$_2$CO$_3$ (18 mmol, 2.48 g) and iodomethane (36 mmol, 2.25 mL), stirred at room temperature for 16 h. The resulting reaction was monitored by TLC. The suspension was filtered off, and the solvent was evaporated, then taken up in 100 mL ethyl acetate. The solution was washed with water, 0.5 N HCl, and brine respectively, dried over anhydrous Na$_2$SO$_4$, filtered and concentrated to give an oily residue. The crude product was purified by flash chromatography on silica gel to afford a light yellow oil product (0.7 g), yield 87%. $^1$H NMR (400 MHz, CDCl$_3$) δ 2.90 (s, 3 H), 3.03 (dd, J=14.8 Hz, 5.6 Hz, 1 H), 3.32 (d, J=14.8 Hz, 11.2 Hz, 1 H), 3.70 (s, 3 H), 4.91 (m, 1 H), 6.91 (d, J=7.6 Hz, 2 H); $^{13}$C NMR (10 MHz, CDCl$_3$) δ 33.8, 52.9, 60.8, 61.1, 92.8, 114.8, 130.9, 136.0 (2 C), 137.9 (2 C), 157.3, 169.2; HRMS (ESI, M+1) cacld for C$_{13}$H$_{14}$F$_3$INO$_3$ 415.9971, found 415.9980.

Example 6

N-Methyl-4-iodophenylalanine (15)

To a solution of 0.7 g (1.69 mmol) of the above product in 50 mL of acetone and water (1:1) was added 0.37 g (2.7 mmol) of K$_2$CO$_3$. The mixture was heated to 45° C. with stirring and kept overnight. After the starting material had disappeared (TLC-monitoring), the reaction solution was concentrated to about half volume, diluted with brine and the pH of the solution was adjusted to 3. The precipitate was collected by filtering, washed with water and THF to give 0.48 g (93%) of a white solid product which was used in the next reaction without further purification.

Example 7

N-Boc-N-methyl-4-iodophenylalanine Methylester (16)

To a solution of NaOH (63 mg, 1.58 mmol) in 25 mL water was added the above product (0.48 g) and stirred to form the solution. Then a solution of Boc$_2$O (6.32 mmol, 1.38 g) in 20 mL alcohol was added and stirred at room temperature for 40 min. The reaction solution was extracted with ethyl acetate (3×20 mL), and the organic phase was combined and washed with water and brine, respectively, dried over Na$_2$SO$_4$, and concentrated under vacuum to yield crude N-Boc-N-methyl-4-iodophenylalanine. This product was dissolved in a mixture of 40 mL acetone and iodomethane (12.64 mmol, 0.79 mL), and anhydrous K$_2$CO$_3$ (0.87 g, 6.32 mmol) was added and stirred for 14 h at room temperature. After this time, the solid was filtered and the solvent was evaporated under reduced pressure. The organic layer was separated, dried over Na$_2$SO$_4$, and concentrated under vacuum to yield 0.64 g of a yellow oil. The crude product was purified by flash chromatography (1:5 ethyl acetate:hexanes) to afford a light yellow oil (0.59 g, 89%). $^1$H NMR (500 MHz, DMSO, 100° C.) δ 1.32 (s, 9 H), 2.66 (s, 3 H), 2.99 (dd, J=14 Hz, 11 Hz, 1 H), 3.16 (dd, J=14 Hz, 5 Hz, 1 H), 3.69 (s, 3 H), 4.59 (m, 1 H), 7.04 (d, J=8 Hz, 2 H), 7.63 (d, J=8 Hz, 2 H); $^{13}$C NMR (125 Hz, CDCl$_3$) 628.3 (3 C), 32.1, 34.7, 52.4, 59.4, 61.6, 92.0, 131.2 (2 C), 137.3, 137.6 (2 C), 171.6, 171.8; HRMS (EI, M) calcd for C$_{16}$H$_{22}$INO$_4$ 419.0588, found 419.0586.

Example 8

Phenylalanine silane linker (2) and N-methyl-phenylalanine silane linker (11). Typically, a solution of N-Boc-4-iodophenylalanine methylester (800 mg, 2 mmol) in NMP (20 mL) was added butyl diethylsilane polystyrene (PE-DES-SiH, 1 g, 1.45 mmol/g) and KOAc (300 mg, 0.3 mmol). The reaction mixture was deaerated by bubbling with a slow stream of argon for 15 min. After the addition of Pd$_2$(dba)$_3$·CHCl$_3$ (110 mg, 0.1 mmol), the reaction flask and reflux condenser were wrapped with aluminum foil, and the mixture was stirred at 110° C. for 24 h. After being cooled to room temperature and washed with CH$_2$Cl$_2$, DMF, 1 N HCl/THF (1:7, 30 min), MeOH, and CH$_2$Cl$_2$, an aliquot of the resin (200 mg) was treated with a solution of Br$_2$ (15 µL) in CH$_2$Cl$_2$ (10 mL) for 20 min. The cleavage solution was filtered and the resin was rinsed with CH$_2$Cl$_2$ (5 mL). Concentration of the combined filtrates gave N-Boc-4-bromophenylalanine methylester.

Example 9

N-Boc-4-bromophenylalanine methylester (the loading level was determined to be 0.1 mmol/g); $^1$H NMR (400 MHz, CDCl$_3$) δ 1.43 (s, 9 H), 3.05 (2 dd, J=6.0 Hz, 13.6 Hz), 3.73 (s, 3 H), 4.57 (m, 1 H), 4.99 (d, J=7.6 Hz, NH, 1 H), 7.01 (d, J=8.0 Hz, 2 H), 7.42 (d, J=8.0 Hz, 2 H); HRMS (ESI, M+1) calcd for C$_{15}$H$_{21}$BrNO$_4$ 358.0648 and 360.0628, found 358.0654 and 360.0635.

Example 10

N-Boc-4-bromophenylalanine methylester (the loading level was determined to be 0.1 mmol/g) (there are s-cis and s-trans isomers). $^1$H NMR (400 MHz, CDCl$_3$) δ 1.32 and 1.37 (2 s, 2×9 H), 2.68 and 2.71 (2 s, 2×3 H), 2.96 (m, 2×1 H), 3.23 (m, 2×1 H), 3.72 and 3.74 (2 s, 2×3 H), 4.46 (m, 2×1 H), 4.87 and 4.89 (2 d, J=5.6, 2×1 H), 7.06 (m, 2×2 H), 7.39 (m, 2×2 H); $^{13}$C NMR (125 Hz, CDCl$_3$) δ 28.3 and 28.4 (2×3 C), 32.1 and 32.9 (2×1 C), 34.6 and 35.1 (2×1 C), 52.4 and 52.5 (2×1 C), 59.5 and 61.6 (2×1 C), 80.3 and 80.6 (2×1 C), 120.6 and 120.7 (2×1 C), 130.9 and 131.0 (2×2 C), 136.6 and 136.9 (2×1 C), 155.0 and 155.9 (2×1 C), 171.4 and 171.7 (2×1 C); HRMS (EI, M) calcd for C$_{16}$H$_{22}$BrNO$_4$ 372.0804 and 374.0784, found 372.0803 and 374.0780.

Example 11

Solid-phase synthesis of sansalvamide A peptide (1 or 1a) and its single N-methyl peptides (alternately any one of 1b-1 k). A suspension of resin 2 (2 g, 0.09 mmol/g) was treated with 50% TFA in CH$_2$Cl$_2$ (20 mL) for 15 min, then washed with CH$_2$Cl$_2$, 0.1 N HCl/THF, MeOH, and DMF. The washed resin was suspended in NMP (20 mL), treated with Boc-R$_2$Leu-OH (5 eq), HATU or HCTU (5 eq), and DIPEA (15 eq) for 6 h. After being washed with DMF, 0.1 N HCl/THF, MeOH, and DMF, the resin was cycled through the same set of conditions for deprotection, washing, coupling, and washing as above using Boc-R$_3$Val-OH (5 eq), Boc-R$_4$Leu-OH (5 eq), and Boc-R$_5$Leu-OH (5 eq) successively in the peptide elongation. (Each of R$_2$-R$_5$ is alternately methyl; R$_1$ can be methyl using resin 2a.) After being washed with DMF, 0.1 N HCl/THF, MeOH, and DMF, the deprotected linear peptide bound to the resin was shaken with LiOH (5 eq) in THF/H$_2$O (7:1, 20 mL) at room temperature for 12 h. After being washed with DMF, 0.1 N HCl/THF, MeOH, and DMF, the resin was treated with 50% TFA in CH$_2$Cl$_2$ (20 mL) for 15 min, then washed with CH$_2$Cl$_2$, 0.1 N HCl/THF, MeOH, and DMF. Cyclization was carried out by treatment of the resin in NMP (20 mL) with PyBOP (5 eq), and DIPEA (15 eq) for 24 h followed by washing with DMF, 0.1 N HCl/THF, MeOH, and CH$_2$Cl$_2$. The resin was then treated with neat TFA for 24 h or with a solution of Br$_2$ in CH$_2$Cl$_2$ at room temperature to release the cyclic peptide or its bromides. The cleavage solution was filtered, and the resin was rinsed with CH$_2$Cl$_2$ (20 mL). Concentration of the combined filtrates gave the crude product, which was filtered through a short silica gel plug with ethyl acetate to afford the corresponding cyclic peptides. Each of compounds 1-1k is characterized as provided in examples 12-12k, respectively.

Example 12

Cyclic Peptide (1) 66% Yield. $^1$H NMR (500 MHz, CD$_3$OD) δ 0.82 (d, J=6.5 Hz, 3 H), 0.85 (d, J=6.5 Hz, 3 H), 0.90 (d, J=6.5 Hz, 3 H), 0.96 (d, J=6.5 Hz, 9 H), 1.00 (d, J=6.0 Hz, 6 H), 1.38-1.41 (m, 1 H), 1.44-1.50 (m, 2 H), 1.63-1.66 (m, 2 H), 1.72-1.75 (m, 2 H), 1.81-2.00 (m, 3 H), 2.04-2.09 (m, 1 H), 3.07 (dd, J=14.0 Hz, 11.0 Hz, 1 H), 4.54 (dd, J=11.0 Hz, 4.5 Hz, 1 H), 3.71 (brs, 1 H), 4.54 (dd, J=11.0 Hz, 4.5 Hz, 1 H), 4.71 (dd, J=9.0 Hz, 5.0 Hz, 1 H), 7.25 (m, 5 H); $^{13}$C NMR (125 MHz, CD$_3$OD) δ 18.6, 20.3, 22.1, 22.2, 22.3, 23.5, 23.6, 23.8, 26.0, 26.3, 26.9, 32.2, 38.0, 39.5, 41.6, 41.9, 52.6, 56.4, 58.2, 60.5, 62.2, 128.0, 129.6, 129.7, 130.3, 138.8, 171.5, 173.0, 173.7, 174.0, 174.1; HRMS (APCI, M+1) calcd for C$_{32}$H$_{52}$N$_5$O$_5$ 586.3969, found 586.3958.

Example 12a

Cyclic Peptide (1a) 68% Yield. $^1$H NMR (500 MHz, CDCl$_3$) δ 0.83 (d, J=7.0 Hz, 3 H), 0.86 (d, J=6.5 Hz, 3 H), 0.89 (d, J=7.0 Hz, 3 H), 0.96 (d, J=7/5 Hz, 9 H), 0.99 (d, J=7.0 Hz, 6 H), 1.37-1.43 (m, 1 H), 1.48-1.50 (m, 2 H), 1.56-1.59 (m, 2 H), 1.70-1.72 (m, 2 H), 1.81-2.00 (m, 3 H), 2.36 (m, 1 H), 3.08 (dd, J=13.0 Hz, 5.5 Hz, 1 H), 3.22 (t, J=7.5 Hz, 1 H), 3.66 (brs, 1 H), 4.03 (t, J=7.5 Hz, 1 H), 4.35 (dd, J=10.5 Hz, 6 Hz, 1 H), 4.42 (t, J=8.0 Hz, 1 H), 4.78 (dd, J=9.0 Hz, 3.0 Hz, 1 H), 7.25 (m, 5 H); $^{13}$C NMR (125 MHz, CD$_3$OD) δ 19.2, 20.8, 22.5, 22.7, 23.0, 23.5, 23.8, 24.0, 26.1, 26.5, 26.9, 32.2, 38.2, 39.4, 41.8, 42.2, 52.4, 56.6, 58.3, 60.5, 62.8, 128.4, 130.8 (2 C), 132.2 (2 C), 135.6, 173.0, 173.7, 174.3, 174.5, 174.8; HRMS (ESI, M+1) calcd for C$_{32}$H$_{51}$BrN$_5$O$_5$ 664.3074 and 666.3054, found 664.3065 and 666.3061.

Example 12b

Cyclic Peptide (1b) 70% Yield. $^1$H NMR (500 MHz, CDCl$_3$) δ 0.77 (d, J=15.5 Hz, 6 H), 0.92-0.97 (m, 18 H), 1.42-1.51 (m, 1 H), 1.53-1.57 (m, 2 H), 1.63-1.67 (m, 2 H), 1.72-1.79 (m, 2 H), 2.18 (brs, 1 H), 2.81 (s, 3 H), 3.02 (dd, J=15.0 Hz, 5.5 Hz, 1 H), 3.14 (t, J=15.0 Hz, 1 H), 3.49 (brs, 1 H), 4.23 (d, J=8.5 Hz, 1 H), 4.43 (d, J=7.0 Hz, 1 H), 4.81 (dd, J=13.0 Hz, 5.5 Hz, 1 H), 5.2 (t, J=15.5 Hz, 1 H), 6.89 (brs, 1 H), 7.17-7.24 (m, 5 H), 7.91 (brs, 1 H), 7.93 (brs, 1 H), 8.08 (d, J=9.0 Hz, 1 H); $^{13}$C NMR (125 MHz, CDCl$_3$) δ 19.7, 19.8, 21.7, 22.5 (2 C), 22.8, 23.1, 23.4, 24.7, 25.2, 25.3, 29.2, 30.9, 37.3, 38.8, 40.5, 40.8, 51.4, 52.4, 54.6, 56.7, 60.3, 127.2, 128.8 (2 C), 129.3 (2 C), 136.4, 171.8, 171.9, 173.2, 173.9, 174.1; HRMS (EI, M$^+$) calcd for C$_{33}$H$_{53}$N$_5$O$_5$ 599.4047, found 599.4048.

Example 12c

Cyclic Peptide (1c) 70% Yield. $^1$H NMR (500 MHz, CDCl$_3$) δ 0.79 (d, J=15.0 Hz, 3 H), 0.85 (d, J=14.5 Hz, 3 H), 0.97 (dd, J=12.0 Hz, 6.0 Hz, 18 H), 1.46-1.56 (m, 2 H), 1.58-1.64 (m, 2 H), 1.66-1.70 (m, 2 H), 1.88-1.91 (m, 1 H), 2.03 (brs, 1 H), 2.87 (s, 3 H), 2.97 (dd, J=12.5 Hz, 5 Hz, 1 H), 3.15 (t, J=12.0 Hz, 1 H), 3.59 (brs, 1 H), 4.32 (d, J=6.0 Hz, 1 H), 4.38 (brs, 1 H), 4.88 (dd, J=12.5 Hz, 5.0 Hz, 1 H), 5.75 (brs, 1 H), 6.93 (brs, 1 H), 7.10 (d, J=8.0 Hz, 2 H), 7.40 (d, J=8.0 Hz, 2 H), 7.62 (brs, 1 H), 7.82 (d, J=8.5 Hz, 1 H). 7.94 (brs, 1 H); $^{13}$C NMR (125 MHz, CDCl$_3$) δ 19.7 (2 C), 21.7, 22.4 (2 C), 22.9, 23.1, 23.4, 24.9, 25.2, 25.4, 29.2, 29.9, 30.9, 37.0, 37.8, 40.2, 40.5, 51.2, 52.3, 56.6, 65.2, 121.2, 131.1 (2 C), 131.9 (2 C), 135.4, 171.6, 172.0, 173.3, 173.4, 174.1; HRMS (EI, M$^+$) calcd for C$_{33}$H$_{52}$BrN$_5$O$_5$ 677.3152 and 679.3131, found 677.3148 and 679.3140.

Example 12d

Cyclic Peptide (1d) 72% Yield. $^1$H NMR (500 MHz, CDCl$_3$) δ 0.86 (d, J=6.0 Hz, 3 H), 0.88 (d, J=7.0 Hz, 3 H), 0.90 (d, J=5.5 Hz, 3 H), 0.94 (dd, J=11.0 Hz, 6.5 Hz, 12 H), 0.99 (t, J=6.5 Hz, 3 H), 1.45-1.50 (m, 2 H), 1.56-1.61 (m, 2 H), 1.74 (brs, 2 H), 1.86-1.92 (m, 1 H), 2.20 (m, 1 H), 3.10 (s, 3 H), 3.22 (dd, J=16.0 Hz, 8 Hz, 1 H), 3.34 (dd, J=16.0 Hz, 6.5 Hz, 1 H), 3.47 (t, J=7.5 Hz, 1 H), 3.68-3.37 (m, 1 H), 3.90 (brs, 1 H), 4.06 (t, J=7.0 Hz, 1 H), 4.33 (brs, 1 H), 4.86 (dd, J=13.5 Hz, 7.0 Hz, 1 H), 6.32 (brs, 1 H), 7.19 (d, J=7.0 Hz, 2 H), 7.28-7.33 (m, 3 H), 7.51 (brs, 1 H), 7.57 (brs, 1 H); $^{13}$C NMR (125 MHz, CDCl$_3$) δ 18.7, 19.7, 22.2, 22.3, 22.6, 22.9 (2 C), 23.1 (2 C), 24.9, 25.0, 26.1, 30.0, 31.8, 36.9, 38.5, 40.0, 41.2, 49.1, 54.3, 59.8, 60.6, 127.5, 129.1 (2 C), 129.3 (2 C), 136.6, 171.8, 172.1, 172.2, 173.0, 173.4; HRMS (ESI, M+1) calcd for $C_{33}H_{54}N_5O_5$ 600.4125, found 600.4117.

Example 12e

Cyclic Peptide (1e) 72% Yield. $^1$H NMR (500 MHz, CDCl$_3$) δ 0.86 (d, J=4.0 Hz, 6 H), 0.89 (d, J=6.5 Hz, 3 H), 0.91-0.96 (m, 12 H), 0.98 (t, J=6.0 Hz, 3 H), 1.40-1.50 (m, 2 H), 1.55-1.62 (m, 2 H), 1.72, (t, J=6.5 Hz, 1 H), 1.89-1.95 (m, 2 H), 2.05-2.08 (m, 2 H), 3.00 (s, 3 H), 3.19 (dd, J=14 Hz, 5 Hz, 1 H), 3.34 (dd, J=14.0 Hz, 9 Hz, 1 H), 3.44 (t, J=7.5 Hz, 1 H), 3.97 (d, J=6.0 Hz, 1 H), 4.09 (t, J=8.0 Hz, 1 H), 4.25-4.31 (m, 1 H), 4.60 (brs, 1 H), 4.84 (t, J=12.0 Hz, H), 6.54 (brs, 1 H), 7.08 (d, J=8.0 Hz, 2 H), 7.42 (d, J=8.0 Hz, 2 H), 7.68 (d, J=8.0 Hz, 1 H), 7.85 (brs, 1 H); $^{13}$C NMR (125 MHz, CDCl$_3$) δ 18.6, 19.6, 22.3 (2 C), 22.5, 22.8, 23.1 (2 C), 24.9, 25.1, 29.9, 30.0, 36.3, 38.4, 38.5, 40.0, 41.2, 49.2, 54.1, 57.6, 59.8, 69.3, 121.4, 131.0 (2 C), 132.1 (2 C), 135.8, 171.0, 171.9, 172.1, 172.9, 173.3; HRMS (EI, M$^+$) calcd for $C_{33}H_{52}BrN_5O_5$ 677.3152 and 679.3131, found 677.3172 and 679.3155.

Example 12f

Cyclic Peptide (1f) 70% Yield. $^1$H NMR (500 MHz, CDCl$_3$) δ 0.78 (d, J=6.5 Hz, 3 H), 0.88 (t, J=5.0 Hz, 12 H), 0.92 (d, J=6.0 Hz, 3 H), 0.97 (t, J=7.0 Hz, 6 H), 1.47-1.51 (m, 1 H), 1.53-1.58 (m, 2 H), 1.65-1.71 (m, 4 H), 1.88 (t, J=6.5 Hz, 1 H), 2.92-2.98 (m, 1 H), 3.16-3.21 (dd, J=14.0 Hz, 8 Hz, 1 H), 3.29 (dd, J=14.0 Hz, 9 Hz, 1 H), 4.02-4.07 (m, 1 H), 4.20 (dd, J=14.5 Hz, 9 Hz, 1 H), 4.41 (dd, J=15.0 Hz, 6 Hz, 1 H), 4.87 (dd, J=15.5 Hz, 8 Hz, 1 H), 6.35 (d, J=6.5 Hz, 1 H), 7.20 (d, J=7.5 Hz, 2 H), 7.25-7.32 (m, 3 H), 7.33 (d, J=6.0 Hz, 1 H), 7.59 (d, J=6.0 Hz, 1 H), 7.69 (d, J=9.5 Hz, 1 H); $^{13}$C NMR (125 MHz, CDCl$_3$) δ 19.5, 20.3, 21.3, 22.2, 22.8, 22.9 (2 C), 23.4, 25.0 (2 C), 25.1, 26.6, 27.6, 30.0, 35.4, 40.2, 40.5, 41.3, 46.6 (2 C), 48.8 (2 C), 52.2, 55.2, 57.4, 127.3, 129.0 (2 C), 129.1 (2 C), 136.8, 170.9, 171.3, 171.8, 172.9, 174.1; HRMS (EI, M+) calcd for $C_{33}H_{53}N_5O_5$ 599.4047, found 599.4042.

Example 12g

Cyclic Peptide (1 g) 70% Yield. $^1$H NMR (500 MHz, CDCl$_3$) δ 0.82 (d, J=6.0 Hz, 3 H), 0.88-0.95 (m, 15 H), 0.97 (dd, J=10.5 Hz, 6.5 Hz, 6 H), 1.49-1.52 (m, 1 H), 1.55-1.58 (m. 2 H), 1.61-1.75 (m, 4 H), 1.87-1.89 (m, 1 H), 2.90 (dd, J=12.5 Hz, 6.5 Hz, 1 H), 3.08 (dd, J=13 Hz, 7 Hz, 1 H), 3.22-3.26 (m, 1 H), 3.99 (dd, J=15 Hz, 6.5 Hz, 1 H), 4.18 (dd, J=14.5 Hz, 6.0 Hz, 1 H), 4.44 (brs, 1 H), 4.88 (dd, J=13.5 Hz, 8.0 Hz, 1 H), 6.3 (brs, 1 H), 7.09 (d, J=8.0 Hz, 2 H), 7.39 (brs, 1 H), 7.42 (d, J=8.0 Hz, 2 H), 7.56 (d, J=9.0 Hz, 1 H), 7.64 (brs, 1 H); $^{13}$C NMR (125 MHz, CDCl$_3$) δ 19.5, 20.3, 21.4, 22.0, 22.7, 23.0 (2 C), 23.3, 24.0, 25.2 (2 C), 27.5, 29.9, 35.2, 40.5, 40.7, 41.4, 48.2, 51.3, 52.4, 55.8, 61.8, 121.1, 131.1 (2 C), 132.0 (2 C), 135.9, 170.8, 171.1, 171.8, 173.1, 173.8; HRMS (EI, M+) calcd for $C_{33}H_{52}BrN_5O_5$ 677.3152 and 679.3131, found 677.3132 and 679.3109.

Example 12h

Cyclic Peptide (1 h) 69% Yield. $^1$H NMR (500 MHz, CDCl$_3$) δ 0.81 (d, J=6.5 Hz, 3 H), 0.84 (dd, J=6.5 Hz, 2 Hz, 12 H), 0.89 (t, J=7.0 Hz, 6 H), 0.92 (d, J=7.0 Hz, 3 H), 1.34-1.40 (m, 2 H), 1.44-1.49 (m, 2 H), 1.51-1.55 (m, 2 H), 1.71-1.76 (m, 1 H), 2.02-2.07 (m, 1 H), 3.07 (dd, J=14.0 Hz, 5 Hz, 1 H), 3.37 (dd, J=14.0 Hz, 6 Hz, 1 H), 3.24 (s, 3 H), 3.44 (t, J=5.5 Hz, 1 H), 4.40 (dd, J=15.5 Hz, 7.5 Hz, 1 H), 4.5 (T, j=10 Hz, 1 H), 4.80-4.84 (m, 1 H), 4.91 (dd, J=15.5 Hz, 9 Hz, 1 H), 5.90 (d, J=8.9 Hz, 1 H), 6.25 (d, J=7.5 Hz, 1 H), 7.17 (d, J=6.3 Hz, 2 H), 7.25-7.29 (m, 3 H), 7.81 (d, J=8.0 Hz, 1 H), 8.68 (d, J=9.5 Hz, 1 H); $^{13}$C NMR (125 MHz, CDCl$_3$) δ 18.1, 19.5, 22.2, 22.6, 22.7 (3 C), 23.2, 23.5, 24.5, 25.1, 25.4, 29.9, 30.6, 37.4, 41.5, 42.2, 51.7, 51.9, 53.5, 55.1, 65.7, 127.3, 128.9 (2 C), 129.6 (2 C), 136.7, 169.6, 170.6, 171.6, 172.3, 172.5; HRMS (ESI, M+1) calcd for $C_{33}H_{54}N_5O_5$ 600.4125, found 600.4115.

Example 12i

Cyclic Peptide (1i) 71% Yield. $^1$H NMR (500 MHz, CDCl$_3$) δ 0.89 (d, J=9.5 Hz, 6 H), 0.92 (d, J=7.0 Hz, 12 H), 0.96 (t, J=7.5 Hz, 6 H), 1.40-1.46 (m, 1 H), 1.58-1.66 (m. 2 H), 1.86-1.93 (m, 4 H), 2.01-2.05 (m, 1 H), 3.08 (brs, 1 H), 3.22 (s, 3 H), 3.43 (brs, 1 H), 3.68-3.70 (m, 1 H), 3.87 (brs, 1 H), 4.21 (brs, 1 H), 4.50 (t, J=8.5 Hz, 1 H), 4.63 (d, J=8 Hz, 1 H), 6.64 (brs, 1 H), 6.84 (brs, 1 H), 7.09 (d, J=7.0 Hz, 2 H), 7.43 (d, J=7.0 Hz, 2 H), 7.48 (brs, 1 H), 7.53 (brs, 1 H); $^{13}$C NMR (125 MHz, CDCl$_3$) δ 18.5, 19.8, 21.9, 22.3 (2 C), 23.0 (2 C), 23.1 (2 C), 24.9, 25.5, 25.6, 29.9, 30.7, 37.8, 39.6, 40.6, 53.5 (2 C), 54.8, 55.6, 67.2, 121.5, 131.1 (2 C), 132.1 (2 C), 135.4, 171.2, 172.5, 173.4, 173.8; HRMS (ESI, M+Na) calcd for $C_{33}H_{52}BrN_5O_5Na$ 700.3052 and 702.3032, found 700.3038 and 702.3022.

Example 12j

Cyclic Peptide (1j) 72% Yield. $^1$H NMR (500 MHz, CDCl$_3$) δ 0.81 (d, J=6.5 Hz, 3 H), 0.85 (d, J=6.5 Hz, 6 H), 089 (t, J=3.0 Hz, 6 H), 0.90 (t, J=6.5 Hz, 6 H), 0.94 (dd, J=6.5 Hz, 4.5 Hz, 3 H), 1.42-1.45 (m, 1 H), 1.49-1.56 (m, 2 H), 1.59-1.64 (m, 2 H), 1.68-1.72 (m, 2 H), 2.08 (brs, 1 H), 2.76 (s, 3 H), 3.17 (dd, J=13.0 Hz, 5.5 Hz, 1 H), 3.32 (t, J=7.5 Hz, 1 H), 3.50 (m, 1 H), 3.66 (dd, J=10.5 Hz, 6 Hz, 1 H), 4.28 (m, 2 H), 4.75 (m, 1 H), 6.64 (brs, 1 H), 6.97 (brs, 1 H), 7.15 (d, J=6.5 Hz, 2 H), 7.23-7.30 (m, 3 H), 7.62 (brs, 1 H), 7.83 (d, J=9.0 Hz, 1 H); $^{13}$C NMR (125 MHz, CDCl$_3$) δ 19.5, 191.9, 21.7, 22.0, 22.5, 22.9, 23.2, 23.3, 25.1, 25.2, 25.3, 27.9, 34.2, 39.7, 40.0, 40.8, 41.0, 48.4, 53.4, 53.5, 60.5, 69.5, 127.4, 129.0 (2 C), 129.1 (2 C), 136.9, 170.4, 172.6 (2 C), 172.7, 174.1; HRMS (EI, M$^+$) calcd for $C_{33}H_{53}N_5O_5$ 599.4047, found 599.4046.

Example 12k

Cyclic Peptide (1k) 71% Yield. $^1$H NMR (500 MHz, CDCl$_3$) δ 0.85 (d, J=6.5 Hz, 3 H), 0.89 (d, J=6.5 Hz, 3 H), 0.92 (d, J=7.0 Hz, 3), 0.94 (d, J=6.0 Hz, 12 H), 0.97 (d, J=6.5 Hz, 3 H), 1.38-1.42 (m, 1 H), 1.48-1.53 (m, 2 H), 1.58-1.61 (m, 2 H), 1.71 (d, J=5.0 Hz, 1 H), 2.38 (brs, 1 H), 2.83 (s, 3 H), 3.18 (dd, J=13.5 Hz, 5.5 Hz, 1 H), 3.46 (t, J=6.5 Hz, 1 H), 3.51-3.56 (m, 1 H), 3.66 (dd, J=9.5 Hz, 5.0 Hz, 1 H), 4.24 (d, J=7.0 Hz, 1 H), 4.32 (dd, J=14.0 Hz, 5.5 Hz, 1 H), 4.79 (m, 1 H), 6.88 (brs, 1 H), 7.06 (d, J=8.5 Hz, 2 H), 7.44 (d, J=8.5 Hz, 2 H), 7.67 (brs, 1 H), 7.77 (d, J=9.0 Hz, 1 H); $^{13}$C NMR (125 MHz, CDCl$_3$) δ 19.2, 19.9, 21.8, 22.2, 22.6, 22.7, 23.1, 23.2, 25.1, 25.3 (2 C), 28.3, 33.9, 39.3, 40.2, 40.8, 41.1, 48.5, 53.4, 53.7, 66.1, 69.9, 121.3, 130.8 (2 C), 132.1 (2 C), 136.0, 170.3, 172.2, 172.5, 172.9, 174.0; HRMS (EI, M$^+$) calcd for $C_{33}H_{52}BrN_5O_5$ 677.3152 and 679.3131, found 677.3150 and 679.3138.

Example 13

The HCT-116 human colon adenocarcinoma screen is a tissue culture first line assay to detect inherent cytotoxicity against malignant cancer cells. This strain is considered to be an "indicator strain" by many for the selection of inhibitors that target solid tumors. The assay is a calorimetric endpoint assay which can be produced in 96-well format trays. Data are acquired by plate reader and dose response curves are produced by computer analysis. Good activity is considered to be $IC_{50}$ values lower than 1 µg/mL. This assay is run routinely as described below and would be understood in the art. Partial results are as provided in Table 1, above.

Materials

1. Media (1000 mL McCoy's 5A Medium, 114 mL Fetal Bovine Serum, 25 mL Hepes buffer solution (IM), 12.5 mL Penicillin-Streptomycin solution)
2. Cell line (HCT-116, human colon cancer cell line)
3. Indicator (MTS and PMS in DPBS)
4. 0.25% Trypsin-EDTA
5. Standard anticancer drug (etoposide (VP-16); stock is 4 mg/mL in DMSO
6. DPBS (without $CaCl_2$ and $MgCl_2$)

Method

Plating Cells

1. Remove medium from the cells and rinse with 10 mL sterile DPBS.
2. Add 5 mL trypsin.
3. Allow to stand in hood for 1 minute.
4. Remove trypsin with sterile pipette.
5. Allow flask to stand in hood for 2-5 minutes.
6. Add 10 mL of media to flask and pipette up and down to gently break up cell clumps.
7. Count the number of cells using a hemacytometer.
8. Determine # of plates needed, and total volume of cell suspension (16 or 18 mL per plate).
9. Dilute cells to a final concentration of $2.5 \times 10^4$ cells/mL in a sterile flask.
10. Pour cell suspension into a sterile trough.

For Serial Dilution Plates

1. Add 175 µL to each well in the first row of a 96 well plate.
2. Add 150 µL to the rest of the wells in A1-A10 & A12.
3. In row 11 add 150 µL cell suspension to the first 6 wells and only media to the last two.

For Single Concentration Plates

1. Add 150 µL of sterile media to G11 & H11.
2. Add 150 µL of cell suspension to all other wells.
3. Add 25 µL more to well H1.

Incubate plates overnight at 37° C. & 5% $CO_2$

Assay

1. Add 25 µL of test compounds @ 10 mg/mL to A1-A10, 25 µL of DMSO to A11 & 25 µL of etoposide (4 mg/mL) to A12.
2. Using a twelve channel pipette, mix well then remove 50 µL from the first row and transfer to the next row, repeat down the plate until row F, then remove tip # 11 and continue down plate discarding the last 50 µL.
3. Incubate plates for 72 h.

Work Up Using MTS

1. Add 20 µL of MTS/PMS solution to each well.
2. Incubate for 3 h.
3. Read plates @490 nm on plate reader.

Example 14a

Given the results of the preceding example, several compounds of this invention were tested against human pancreatic cancer cell lines. Two cancer cell lines were selected: S2-013 (well-differentiated) and AsPC-1 (poorly differentiated). These cell lines were purchased from American Type Culture Collection (Manassas, Va.). Both cell lines were grown in DMEM and plated as monolayers in the medium supplemented with 10% fetal bovine serum in a humidified atmosphere of 95% $O_2$ and 5% $CO_2$ at 37° C. The cells were regularly seeded into 75 cm² flasks with media changes every second or third day. For experiments, cells were grown to 70% confluence, digested with trypsin-EDTA, and plated in either 6-, 24-, or 48-well plates.

Example 14b

DNA Synthesis by [methyl-³H] Thymidine Incorporation. Cells were plated in 24-well plates at a concentration of 50,000 cells/well. After reaching 50% confluence, they were incubated in serum-free medium for 24 hours, which was then replaced with fresh serum-free medium with or without treatment with 10 µM of each of cyclic peptides 1-1k (#'s 1-12 in FIG. 5), sansalvamide A (#13 in FIG. 5) and scytalidamide A (#14 in FIG. 5). After the required period of culture, cellular DNA synthesis was assayed by adding 0.5 Ci ³H-methyl thymidine/well and incubating cells for another 6 hours. The cells were then washed twice with PBS, fixed with 10% trichloroacetic acid, and solubilized by adding 250 µl of 0.4 M NaOH to each well. Radioactivity, indicating incorporation of ³H-methyl thymidine into DNA, was measured by adding scintillation cocktail and counting on a scintillation counter (LKB RackBeta; Wallac, Turku, Finland).

Figure 5:
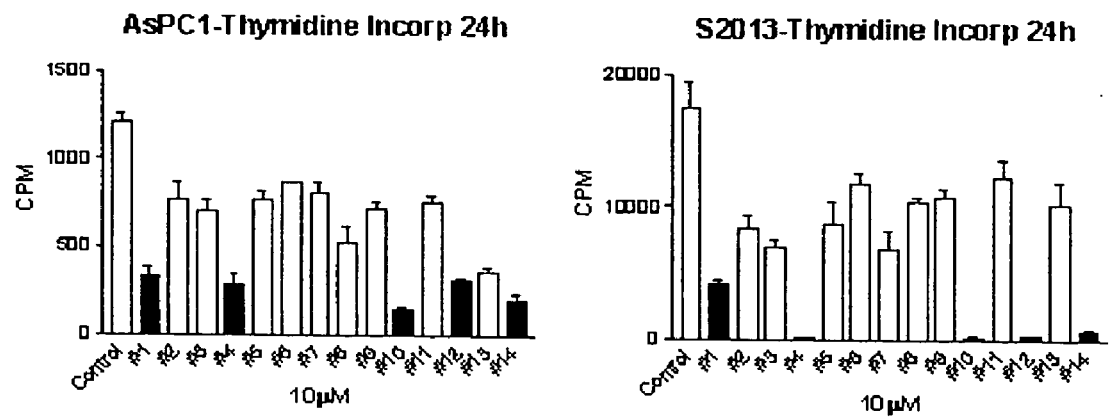
FIG. 5. Effect of sansalvamide analogues on proliferation of human pancreatic cancer cells (AsPC-1 and S2013) measured by thymidine incorporation.
Figure 6:
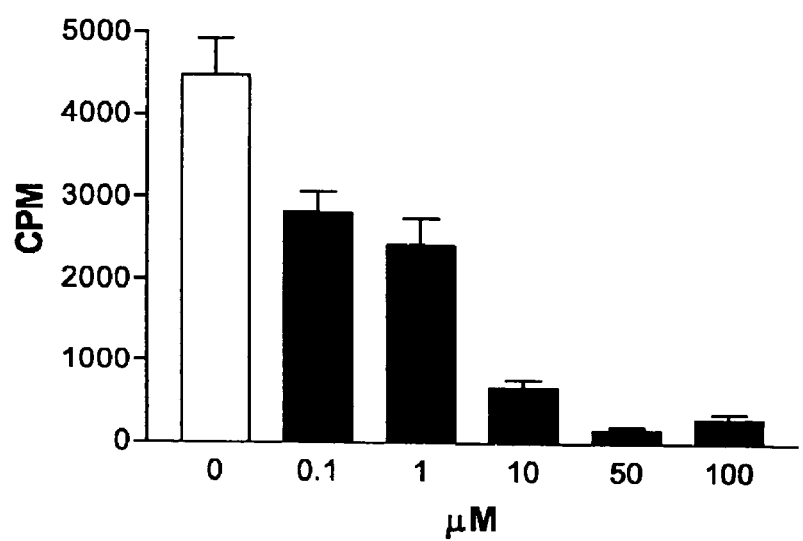
FIG. 6. Concentration-dependent effects of analogue 1k on thymidine incorporation of AsPC-1 cells at 24 hours.

All of the peptide analogues and the two parent compounds (#'s 13&14), caused inhibition of thymidine incorporation in both AsPC-1 and S2-013 human pancreatic cancer cells (FIG. 5). At a concentration of 10 µM, the most dramatic effects were seen with compounds 1, 1c, 1i, 1k and scytalidamide A, all of which caused greater than 50% inhibition at 24 hr. Cyclic peptide compound 1k a concentration-dependent inhibition of thymidine incorporation in AsPC-1 cells at 24 hours (FIG. 6). Similar effects of compound 1k were seen in S2013 cells. Compounds 1c and 1i showed similar effects on thymidine incorporation in AsPC-1 and S2O13 cells.

Example 14c

Morphological Changes Using Light Microscopy. AsPC-1 and S2-013 cells plated in 24-well plates were treated with varying concentrations (0.1-100 µM) of cyclic peptide 1k for 24 hours. Cells were then viewed using light microscopy, and digital images were taken with a Kodak DC120 zoom digital camera (Eastman Kodak Co., Rochester, N.Y.).

With the use of light microscopy, obvious morphological changes could be seen at compound concentrations of 10 µM or more in AsPC-1 cells. Similar effects of compound 1k were seen in S2013 cells. Analogues 1c and 1i showed similar effects on cellular morphology of AsPC-1 and S2013 cells. The changes seen, including rounding up of the cells, nuclear condensation and detachment from the plate, show that the cells are undergoing apoptosis.

Example 14d

Cell Proliferation Assay. Cells were regularly seeded into three 6-well plates and incubated at 37° C. for 24 hours. Cells were then cultured in serum-free medium for another 24 hours and treated in fresh serum-free medium with or without 10 μM of cyclic peptide 1k for 24, 48, and 72 hours. At the end of each time period, the cells were trypsinized to produce a single cell suspension, and the cell number in each well was determined using Guava Technologies=ViaCount Assay (Guava Technologies Inc, Hayward, Calif.). Using 10 μM of cyclic peptides compounds 1i and 1k (and scytalidamide A), a decrease in cell number was seen in cells treated with peptide while those treated with vehicle (DMSO) alone continued to grow. Each peptide analyzed caused a significant ($p<0.05$) decrease in the number of cells at 72 hours, the exception being use of scytalidamide A in the S2-013 cell line.

An indication that the peptides are not cytotoxic to the cells is the fact that the percentage of viable AsPC-1 cells did not change despite a significant decrease in the number of cells treated with the cyclic peptide. Similar effects were seen in S2013 cells.

Example 14e

Cell Cycle Analysis by Flow Cytometry. AsPC-1 and S2013 human pancreatic cancer cells were cultured in T75 flasks with media containing 10% FBS. After reaching 50-60% confluence, the cells were serum-starved for 24 hours, and then treated with 10 μM of cyclic peptide 1k for 24 hours. At the end of the treatment, the cells were harvested with trypsin-EDTA solution to produce single cell suspension. The cells were then centrifuged at 1000×g for 10 minutes. The pellets were washed twice with ice-cold phosphate buffer saline (PBS), and re-suspended in 0.5 ml PBS. 5 ml of ice-cold 70% ethanol was added to each cell suspension and incubated for 12 hours at 4° C. The cells fixed in ethanol were centrifuged at 1000×g for 10 minutes and the subsequent pellets were washed with ice-cold PBS twice. The final cell pellets were reconstituted in the 1 ml Telford reagent and horizontally shaken for 1 hour in the dark at room temperature. The red fluorescence of the single events was recorded using a laser beam at 488 nm excitation 8 and 610 nm as emission 8 to measure the DNA index. Experiments were repeated three times. The cyclic peptide 1k caused G0/G1 phase cell cycle arrest in both cell lines tested. This was accompanied by a marked decrease in the S phase fraction and an increase in the subG1 fraction of apoptotic cells.

Example 14f

Statistical Analysis. Data were analyzed by ANOVA with Dunnett's or Bonferoni's corrections for multiple comparisons, as appropriate. This analysis was performed with the Prism software package (GraphPad, San Diego, Calif.). Data were expressed as mean±SEM.

Example 15

The PC-3, LNCaP, and DU145 human prostate cancer cell lines are used in an assay that measures [$^3$H]thymidine incorporation (DNA synthesis). Briefly, as known in the art, the cells are maintained in an RPMI-1640 medium with 10% fetal bovine serum (FBS). The cells are plated into 24-wells (about 20,000 per plate) in the 1640/10% FBS medium, and the cells continue to culture to subconfluence. The medium is changed to serum free 1640 medium for serum starvation for 24 h, then cell growth is stopped in the $G_0$ phase. Serum is again added to stimulate cell growth to the S phase in the presence of [$^3$H]thymidylate. To test the effect of the present compounds in the serum-induced proliferation, the medium is changed to a serum-free medium (control), or serum-free medium supplemented with FBS (5%), or serum-free medium with FBS (5%) containing the particular compound. Results are as provided in Table 3 for PC-3, MDA-MB231 (breast cancer) and WM115 (melanoma) cell lines.

TABLE 3

Cell Proliferation Assays.
Fold Induction Over DMSO control

| Compound (conc) | | PC-3 (Prostate) | Cell Lines MDA-MB231 (Breast) | WM115 (Melanoma) | |
| --- | --- | --- | --- | --- | --- |
| 1 | (1 μM) | 1.03 | 0.91 | 0.92 | |
|   | (10 μM) | 0.90 | 0.69 | 0.56 | |
| 1a | (1 μM) | 0.94 | 0.95 | 0.85 | |
|   | (10 μM) | 0.74 | 0.60 | 0.99 | |
| 1b | (1 μM) | 1.24 | 0.87 | 1.02 | |
|   | (10 μM) | 0.81 | 0.71 | 3.02 | |
| 1c | (1 μM) | 0.75 | 0.56 | 1.10 | |
|   | (10 μM) | 0.11 | 0.09 | 0.32 | |
| 1d | (1 μM) | 0.63 | 1.09 | 0.87 | |
|   | (10 μM) | 0.52 | 0.91 | 0.98 | |
| 1e | (1 μM) | 0.62 | 1.20 | 0.89 | |
|   | (10 μM) | 0.82 | 0.82 | 0.95 | |
| 1f | (1 μM) | 0.92 | 1.04 | 1.00 | |
|   | (10 μM) | 0.74 | 0.26 | 1.06 | |
| 1g | (1 μM) | 0.74 | 0.88 | 1.02 | |
|   | (10 μM) | 0.67 | 0.31 | 0.84 | |
| 1h | (1 μM) | 0.79 | 1.01 | 1.13 | |
|   | (10 μM) | 0.64 | 0.28 | 0.51 | |
| 1i | (1 μM) | 0.85 | 0.96 | 1.44 | |
|   | (10 μM) | 0.19 | 0.07 | 0.05 | |
| 1j | (1 μM) | 0.86 | 0.78 | 1.75 | |
|   | (10 μM) | 0.8 | 0.82 | 0.60 | |
| 1k | (1 μM) | 0.95 | 3.17 | 1.05 | |
|   | (10 μM) | 0.66 | 0.41 | 0.13 | |
| Scytalidamide A | | 0.63 | 2.75 | 1.01 | ⎫ Natural |
| (10 μM) | | 0.15 | 0.11 | 0.07 | ⎬ Products |
| Sansalvamide A | | 0.95 | 0.90 | 0.98 | ⎭ Reference |
| (10 μM) | | 0.22 | 0.09 | 0.02 | |

Example 16

Cell proliferation assays with human prostate (PC-3), breast (MDA-MB231) and melanoma (WM-115) cancer cell lines were performed as reported in the literature, tested against compounds 1-1k and natural product references sansalvamide A and scytalidamide A. The compounds were dissolved in DMSO, and diluted for cell culture to the concentrations listed in Table 3, below. Cells were plated at 5,000 cells per well in 24-well plates, treated for three days, then counted. Cell number was normalized to the number of cells in untreated control (DMSO) cells, also after three days. Compounds 1c and 1i inhibited all three cells lines at 10 μM. Associated time course studies showed that a 24-hour exposure in PC-3 and a 6-12-hour exposure in WM-115 produced a half-maximal inhibition.

The ability of the compounds in this invention to induce apoptosis was also studied, based on a methodology previously reported in the literature. (See, Soff et al. *Cancer Res.*, 63:4275-4289, 2003.) As understood by those skilled in the art, the ability of Annexin V to bind two cells is related to altered phospholipids on a cell surface, induced by apoptosis. As such, increased Annexin V binding indicates induction of apoptosis. After 72 hours, induction of apoptosis was observed in PC-3 cells after treatment with compound 1i.

Caspase-3 is a mediator of apoptosis, and induction of Caspase-3 activity indicates induction of apoptosis. Activity of Caspase-3 was measured by a fluorometric assay, as described in the literature, referenced above. It was observed that Caspase-3 activity in PC-3 cells was induced by compounds 1c and 1i, relative to DMSO and staurosporin controls.

We claim:

1. A cyclic peptide compound of a formula

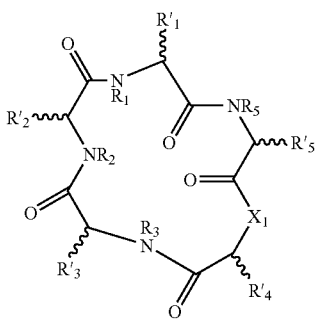

wherein each of $R_1$-$R_5$ is independently selected from H and alkyl moieties; $X_1$ is selected from O and $NR_4$; $R_1'$ is $X_2ArCH_2$—, wherein $X_2$ is selected from Br, Cl and alkyl, and Ar is selected from aryl and heteroaromatic moieties; and
each of $R_2'$-$R_5'$ is independently selected from $R_1'$, $CH_3$—, $(CH_3)_2CH$—, $(CH_3)_2CHCH_2$—, $CH_3CH_2(CH_3)CH$— and $CH_3S\ CH_2CH_2$— moieties.

2. The compound of claim 1 wherein $X_1$ is $NR_4$, $R_1'$ is $X_2ArCH_2$—, and $X_2$ is Br.

3. The compound of claim 2 wherein each of $R_2'$-$R_5'$ is independently selected from $(CH_3)_2CHCH_2$— and $(CH_3)_2CH$—.

4. The compound of claim 3 wherein at least one of $R_1$-$R_5$ is alkyl.

5. The compound of claim 2 wherein each of $R_2'$, $R_4'$ and $R_5'$ are $(CH_3)_2CHCH_2$— and $R_3'$ is $(CH_3)_2CH$—.

6. The compound of claim 5 wherein $R_1'$-$R_5'$ are syn.

7. The compound of claim 6 wherein at least one of $R_1$-$R_5$ is methyl.

8. An antitumor compound of a formula

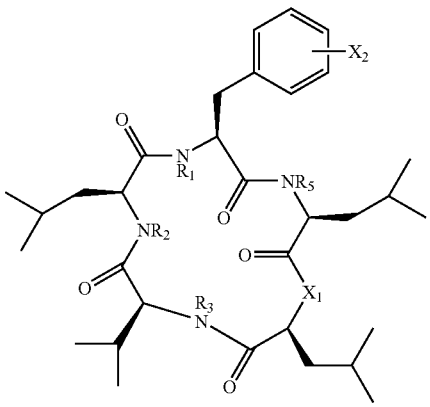

wherein each of $R_1$-$R_5$ is independently selected from H and alkyl moieties; $X_1$ is $NR_4$ where $X_2$ is selected from Br, Cl and alkyl; and $X_1$ is O where $X_2$ is selected from halide and alkyl.

9. The compound of claim 8 wherein $X_1$ is $NR_4$.

10. The compound of claim 9 wherein at least one of $R_1$-$R_5$ is alkyl.

11. The compound of claim 10 wherein at least one of $R_1$-$R_5$ is methyl.

12. The compound of claim 11 wherein $X_1$ is $NR_4$ and wherein $X_2$ is Br.

* * * * *

UNITED STATES PATENT AND TRADEMARK OFFICE
CERTIFICATE OF CORRECTION

| | | |
|---|---|---|
| PATENT NO. | : 7,709,443 B2 | Page 1 of 1 |
| APPLICATION NO. | : 10/962168 | |
| DATED | : May 4, 2010 | |
| INVENTOR(S) | : Richard B. Silverman et al. | |

It is certified that error appears in the above-identified patent and that said Letters Patent is hereby corrected as shown below:

Column 16, Line 45:

"628.3" should read --δ 28.3--

Signed and Sealed this
Nineteenth Day of April, 2011

David J. Kappos
*Director of the United States Patent and Trademark Office*